US009447421B2

(12) United States Patent
Geijskes et al.

(10) Patent No.: US 9,447,421 B2
(45) Date of Patent: *Sep. 20, 2016

(54) **METHODS FOR *AGROBACTERIUM*-MEDIATED TRANSFORMATION OF SUGAR CANE**

(75) Inventors: Robert Jason Christopher Geijskes, Research Triangle Park, NC (US); Paulo Cezar De Lucca, Research Triangle Park, NC (US)

(73) Assignees: Syngenta Participations AG, Basel (CH); Queensland University of Technology, Brisbane (AU)

( * ) Notice: Subject to any disclaimer, the term of this patent is extended or adjusted under 35 U.S.C. 154(b) by 332 days.

This patent is subject to a terminal disclaimer.

(21) Appl. No.: 13/703,846

(22) PCT Filed: Jun. 22, 2011

(86) PCT No.: PCT/US2011/041333
§ 371 (c)(1),
(2), (4) Date: Feb. 13, 2013

(87) PCT Pub. No.: WO2011/163292
PCT Pub. Date: Dec. 29, 2011

(65) Prior Publication Data
US 2013/0152232 A1 Jun. 13, 2013

Related U.S. Application Data

(60) Provisional application No. 61/407,584, filed on Oct. 28, 2010, provisional application No. 61/358,148, filed on Jun. 24, 2010.

(51) Int. Cl.
*C12N 15/82* (2006.01)
*A01H 4/00* (2006.01)

(52) U.S. Cl.
CPC ............. *C12N 15/8205* (2013.01); *A01H 4/00* (2013.01); *C12N 15/8201* (2013.01)

(58) Field of Classification Search
CPC .................................................. C12N 15/8205
USPC ................ 435/469, 252.2, 320.1, 430.1, 480
See application file for complete search history.

(56) References Cited

U.S. PATENT DOCUMENTS

| 5,563,055 | A | 10/1996 | Townsend et al. |
| 5,981,840 | A | 11/1999 | Zhao et al. |
| 7,045,357 | B2 * | 5/2006 | Cheng et al. .................. 435/469 |
| 8,742,202 | B2 * | 6/2014 | Zhong ........................... 800/278 |
| 2001/0054186 | A1 * | 12/2001 | Cheng ................ C12N 15/8205 800/278 |
| 2004/0237133 | A1 | 11/2004 | Goldman et al. |
| 2006/0130175 | A1 | 6/2006 | Ellis et al. |
| 2008/0118981 | A1 | 5/2008 | Akula et al. |
| 2008/0118987 | A1 | 5/2008 | Eastwood et al. |

FOREIGN PATENT DOCUMENTS

| CN | 101768604 A | 7/2010 |
| WO | WO 00/34491 A2 | 6/2000 |
| WO | WO 2010/068521 A1 | 6/2010 |
| WO | WO 2010/151634 A1 | 12/2010 |

OTHER PUBLICATIONS

Praveen et al. 2015. SGBD: A Sugarcane Germplasm Database. Sugar Tech 17: 150-155.*
Sy and Eh. 2013. Development of a DNA fingerprinting database and cultivar identification in sugarcane using a genetic analyser. Proc S Afr Sug Technol Ass 86: 200-212.*
Lu et al. 1994. Molecular diversity and genome structure in modern sugarcane varieties. Euphytica 78: 217-226.*
Bischoff and Gravois. 2004. The development of new sugarcane varieties at the LSU Agcenter. Journal American Society Sugar Cane Technologist 24: 142-164.*
Arencibia et al. 1998. An efficient protocol for sugarcane transformation mediated by Agrobacterium tumefaciens. Transgenic Research 7: 213-222.*
Birch. 1997. Plant transformation: Problems and strategies for practical application. Annu Rev Plant Physiol Plant Mol Biol 48: 297-326.*
Enriquez-Obregon et al., "Herbicide-resistant sugarcane (*Saccharum officinarum* L.) plants by *Agrobacterium*-mediated transformation", *Planta* (1998) 206: 20-27.
Li et al., "Study on Genetic Transformation of Sugarcane Mediated by Agrobacterium Tumefaciens", *Acta Agriculturae Jiangxi* (2006) 18(2):22-25.
Extended European Search Report in corresponding European Patent Application No. 11798792,5; Mailed: Oct. 10, 2013, 6 pages.
Jingping et a., "GFP Gene Transformation of Sugarcane Mediated by *Agrobacterium tumefaciens*," Chinese Journal of Tropical Crops, vol. 24, No. 4, pp. 23-25, Dec. 2003.
Zizhang, et al., "Genetic Transformation of Sugarcane (*Saccharum officinarum*) Mediated by *Agrobacterium tumefaciens*," Journal of Agricultural Biotechnology, Oct. 2002, pp. 237-240.
Elliott A.R. et al., "*Agrobacterium*-mediated transformation of sugarcane using GFP as a screenable marker", *Aust. J. Plant Physiol.*, 1998, vol. 25, 739-743.
Joyce P. et al., "Selection system and co-cultivation medium are important determinants of *Agrobacterium*-mediated transformation of sugarcane", *Plant Cell Rep*, 2010, 29:173-183.

(Continued)

*Primary Examiner* — Anne Kubelik
*Assistant Examiner* — Karen Redden
(74) *Attorney, Agent, or Firm* — Myers Bigel & Sibley, P.A.

(57) ABSTRACT

The present invention provides methods for *Agrobacterium*-mediated transformation of sugar cane (*Saccharum* spp.) comprising introducing a nucleotide sequence of interest into a sugar cane callus tissue or cell thereof via *Agrobacterium* mediated delivery, wherein the sugar cane callus tissue is less than 28 days post-initiation. The invention further provides methods for transforming a sugar cane callus tissue or cell thereof comprising inoculating the sugar cane callus tissue that is less than 28 days post-initiation with an *Agrobacterium* comprising a nucleotide sequence of interest to produce an *Agrobacterium*-inoculated sugar cane tissue or cell thereof; and co-cultivating the *Agrobacterium* and the sugar cane callus tissue to produce a transformed sugar cane callus tissue or cell thereof.

4 Claims, No Drawings

(56) References Cited

OTHER PUBLICATIONS

Notification of Transmittal of International Preliminary Report on Patentability in corresponding International Application No. PCT/US2011/041333, mailed Dec. 28, 2012 (7 pages).
Anderson and Birch, *Tropical Plant Biology*, 2012; 5(2)183-192.
Arencibia A.D. et al., "An efficient protocol for sugarcane (*Saccharum* spp. L.) transformation mediated by *Agrobacterium tumefaciens*" *Transgenic Research*, vol. 7, 1998, pp. 231-222.
Arencibia A.D. et al., "Sugarcane (*Saccharum* spp.)", *Methods in Molecular Biology*, vol. 344, *Agrobacterium Protocols*, 2/e vol. 2, ed. Wang ($2^{nd}$ ed., Humana Press, Inc.), 2007, pp. 227-235.
Benguela et al., *Biotecnología Aplicada*, 2011, vol. 28 (4):216-220.
Cheng M. et al., "Desiccation of Plant Tissues Post-*Agrobacterium* Infection Enhances T-DNA Delivery and Increases Stable Transformation Efficiency in Wheat", *In Vitro Cell. Dev. Biol.—Plant*, Nov.-Dec. 2003, vol. 39, pp. 595-604.
Cheng M. et al., "Factors Influencing *Agrobacterium*-Mediated Transformation of *Monocotyledonous* Species", *In Vitro Cell. Dev. Biol.—Plant*, 40:31-45, Jan.-Feb. 2004.
de la Riva G.A. et al., "*Agrobacterium tumefaciens*: a natural tool for plant transformation", *Electronic Journal of Biotechnology*, vol. 1, No. 3, Dec. 15, 1998, pp. 118-133.
Extended European Search Report in corresponding European Patent Application No. 1079642.0, mailed Nov. 21, 2013, 6 pages.
Finer, John J., "Plant Nuclear Transformation", *Springer*, 2010, pp. 3-7.
Gonzalez et al., Efficient regeneration and *Agrobacterium tumefaciens* mediated transformation of recalcitrant sweet potato (*Ipomoea batatas* L.) cultivars., *Asia Pacific J. Mol. Biol. Biotechnol.*, 2008, 16(2):25-33.
International Search Report and Written Opinion of International Application No. PCT/US2010/039774, mailed Aug. 27, 2010, 10 pages.
Lakshmanan P. et al., "Invited Review: Sugarcane Biotechnology: The Challenges and Opportunities", *In Vitro Cell. Dev. Biol.—Plant*, Jul.-Aug. 2005, vol. 41, pp. 345-363.
Manickavasagam M. et al., "*Agrobacterium*-mediated genetic transformation and development of herbicide-resistant sugarcane (*Saccharum* species hybrids) using axillary buds", *Plant Cell Rep*, 2004, vol. 23, pp. 134-143.

Non-Final Office Action Corresponding to U.S. Appl. No. 13/378,497, Date of Mailing: Jun. 24, 2014, 19 pages.
Opabode J.T. et al., "Agrobacterium-mediated transformation of plants: emerging factors that influence efficiency", *Biotechnology and Molecular Biology Review*, vol. 1 (1), Apr. 2006, pp. 12-20.
Patel et al., "Enhancing Agrobacterium tumefaciens-mediated transformation efficiency of perennial ryegrass and rice using heat and high maltose treatments during bacterial infection", *Plant Cell Tiss. Organ Cult.*, 2013, 114:19-29.
Rasul et al., *Int. J. Agric. Biol.*, 2014, 16:1147-1152.
Scortecci et al., *Challenges, Opportunities and Recent Advances in Sugarcane Breeding*, in *Plant Breeding*, Dr. Ibrokhim Abdurakhmonov (Ed.), 2012, InTech, Available from: http://www.intechopen.com/books/plant-breeding/challenges-opportunities-and-recent-advances-insugarcane-breeding.
Vogel J. et al., "High-efficiency *Agrobacterium*-mediated transformation of *Brachypodium distachyon* inbred line Bd21-3", *Plant Cell Rep*, 2008, 27:471-478.
Zhang S.Z. et al., "Expression of the *Grifola frondosa* Trehalose Synthase Gene and Improvement of Drought-Tolerance in Sugarcane (*Saccharum officinarum* L.)", *Journal of Integrative Plant Biology*, 2006, vol. 48, No. 4, pp. 453-459.
Pitzschke, Andrea "Agrobacterium infection and plant defense—transformation success hangs by a thread," *Frontiers in Plant Science*, Dec. 18, 2013, 12 pages.
Krishnan, Subramanian Radhesh et al., "Rapid regeneration and ploidy stability of 'cv IR36' indica rice (*Oryza sativa*. L) confers efficient protocol for in vitro callus organogenesis and *Agrobacterium tumefaciens* mediated transformation," *Botanical Studies* 2013, 54:47, 12 pages.
"Sugar Research Australia," *Sugarcane Varieties, International Society of Sugarcane Technologists*, accessed website on Feb. 19, 2016: http://www.sugarcanevariety.org/CountryDetails.aspx?CountryID=2; 6 pages.
Wu, Luguang et al., "Doubled sugar content in sugarcane plants modified to produce a sucrose isomer." *Plant Biotechnology Journal* (2007), pp. 109-117.
Grof, Christopher et al., "Temperature effect on carbon partitioning in two commercial cultivars of sugarcane," *Functional Plant Biology*, 2010, 37; pp. 334-341.

* cited by examiner

METHODS FOR AGROBACTERIUM-MEDIATED TRANSFORMATION OF SUGAR CANE

STATEMENT OF PRIORITY

This application is a 35 U.S.C. §371 national phase application of International Application Serial No. PCT/US2011/041333, filed Jun. 22, 2011, which claims the benefit, under 35 U.S.C. §119 (e), of U.S. Provisional Application No. 61/407,584; filed Oct. 28, 2010, and U.S. Provisional Application No. 61/358,148, filed Jun. 24, 2010, the entire contents of which are incorporated by reference herein.

FIELD OF THE INVENTION

The invention relates generally to plant molecular biology, particularly methods for *Agrobacterium*-mediated transformation of sugar cane.

BACKGROUND

Sugar cane (*Saccharum* spp.) is a highly polyploid plant grown in different parts of the world from the tropics to the subtropics, and accounts for around 60% of the world's sugar. It is also one of the important cash crops in many developing/developed countries, with a high trade value. The importance of sugar cane has increased in recent years because cane is an important raw material for sugar industries and allied industries producing alcohol, acetic acid, butanol, paper, plywood, industrial enzymes and animal feed. Considering its importance in the agricultural industry, concerted efforts are being made for its improvement using biotechnological approaches.

*Agrobacterium tumefaciens* is a soil-borne pathogen that is widely used to introduce heterologous polynucleotides into plant cells, including plant cells from sugar cane. *A. tumefaciens* transfers a particular polynucleotide segment of a tumor-inducing (Ti) plasmid into the nucleus of infected host cells, which subsequently stably integrates into the host's genome. Advantageously, heterologous polynucleotides can be placed between the borders of the Ti plasmid, or plasmid modified for this purpose, and transferred to plant cells.

Although *Agrobacterium*-mediated transformation has been used for genetic manipulation of sugar cane, efficiency and reproducibility of the available methodologies continue to be a challenge. In fact, *A. tumefaciens* induces necrosis in cultured, transformed sugar cane tissue, with a resultant low transformation frequency (Arencibia et al. (1998) *Transgenic Res.* 7:123-222; Enriquez-Obregón et al. (1997) *Biotecnologia Aplicada* 14:169-174; and de la Riva et al. (1998) *Electron. J. Biotechno.* 1:118-133).

Because of the importance of manipulating sugar cane for improved characteristics (e.g., increased resistance to biotic or abiotic stresses, or improved production), there is a need for additional methods that advantageously increase the efficiency of *Agrobacterium*-mediated transformation of this important agricultural crop.

Accordingly, the present inventors have overcome the deficiencies of the prior art by providing methods of *Agrobacterium*-mediated transformation of sugar cane that result in greater transformation efficiencies

SUMMARY OF THE INVENTION

Methods for *Agrobacterium*-mediated transformation of sugar cane (*Saccharum* spp.) are provided wherein very young sugar cane tissue or a cell thereof is transformed using *Agrobacterium*-mediated transformation.

Accordingly, a first aspect of the invention provides a method of transforming a sugar cane callus tissue or a cell thereof, the method comprising introducing a nucleotide sequence of interest into a sugar cane callus tissue or a cell thereof via *Agrobacterium*-mediated delivery, wherein the sugar cane callus tissue is less than 28 days post-initiation.

A second aspect of the invention provides a method of transforming a sugar cane tissue and/or cell thereof, the method comprising: (a) inoculating a sugar cane tissue or a cell thereof that is less than 28 days post-initiation with *Agrobacterium* comprising a nucleotide sequence of interest, to produce an *Agrobacterium*-inoculated sugar cane tissue or cell thereof; and (b) co-cultivating the *Agrobacterium*-inoculated sugar cane tissue or a cell thereof to produce a transformed sugar cane callus tissue or cell thereof.

In a further aspect, the present invention provides a method of transforming a sugar cane tissue and/or cell thereof, the method comprising: (a) inoculating a sugar cane tissue or a cell thereof that is less than 28 days post-initiation with *Agrobacterium* comprising a nucleotide sequence of interest, to produce an *Agrobacterium*-inoculated sugar cane tissue or cell thereof; and (b) co-cultivating the *Agrobacterium*-inoculated sugar cane tissue or a cell thereof to produce a transformed sugar cane callus tissue or cell thereof, wherein transformation efficiency is increased.

In additional aspects, the present invention provides a method of transforming a sugar cane tissue and/or cell thereof, the method comprising: (a) inoculating a sugar cane tissue or a cell thereof that is less than 28 days post-initiation with *Agrobacterium* comprising a nucleotide sequence of interest, to produce an *Agrobacterium*-inoculated sugar cane tissue or cell thereof; and (b) co-cultivating the *Agrobacterium*-inoculated sugar cane tissue or a cell thereof to produce a transformed sugar cane callus tissue or cell thereof, wherein regeneration of sugar cane plants is increased.

In other aspects, the present invention provides a method of transforming a sugar cane tissue and/or cell thereof, the method comprising: (a) inoculating a sugar cane tissue or a cell thereof that is less than 28 days post-initiation with *Agrobacterium* comprising a nucleotide sequence of interest, to produce an *Agrobacterium*-inoculated sugar cane tissue or cell thereof; and (b) co-cultivating the *Agrobacterium*-inoculated sugar cane tissue or a cell thereof to produce a transformed sugar cane callus tissue or cell thereof; wherein nucleic acid delivery is increased.

DETAILED DESCRIPTION OF THE INVENTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

The present invention is directed to *Agrobacterium*-mediated transformation methods comprising the use of young sugar cane tissue and/or cells thereof that may allow for increased efficiency of transfer of a nucleotide sequence of interest from the *Agrobacterium* into the inoculated sugar cane tissue and/or cells. The present inventors have surprisingly discovered that using young tissue of sugar cane for *Agrobacterium*-mediated transformation results in increased transformation efficiency and/or increased regeneration of transformed sugar cane plants. Another benefit is that the tissue produced using these methods may reduce the time required for transformation—meaning that it may take less time to generate transgenic plants and is a benefit that might not be measured as an increase in transformation efficiency.

Accordingly, a first aspect of the invention provides a method of transforming a sugar cane callus tissue or a cell thereof, the method comprising introducing a nucleotide sequence of interest into a sugar cane callus tissue or a cell thereof via *Agrobacterium*-mediated delivery, wherein the sugar cane callus tissue is less than 28 days post-initiation.

A second aspect of the invention provides a method of transforming a sugar cane tissue and/or cell thereof, the method comprising: (a) inoculating a sugar cane tissue and/or cell thereof that is less than 28 days post-initiation with an *Agrobacterium* comprising a nucleotide sequence of interest, to produce an *Agrobacterium*-inoculated sugar cane tissue or cell thereof; and (b) co-cultivating the *Agrobacterium*-inoculated sugar cane tissue or a cell thereof to produce a transformed sugar cane callus tissue or cell thereof.

Unless the context indicates otherwise, it is specifically intended that the various features of the invention described herein can be used in any combination.

As used herein, "about" means within a statistically meaningful range of a value such as a stated concentration range, time frame, weight (e.g., a percentage change (reduction or increase in weight), volume, temperature or pH. Such a range can be within an order of magnitude, typically with 20%, more typically still within 10%, and even more typically within 5% of a given value or range. The allowable variation encompassed by "about" will depend upon the particular system under study, and can be readily appreciated by one of skill in the art.

As used herein, "a," "an" or "the" can mean one or more than one. For example, "a" cell can mean a single cell or a multiplicity of cells.

As used herein, "and/or" refers to and encompasses any and all possible combinations of one or more of the associated listed items, as well as the lack of combinations when interpreted in the alternative ("or").

As used herein, the term "polypeptide" encompasses both peptides and proteins, unless indicated otherwise.

As used herein, an "isolated" polypeptide or polypeptide fragment means a polypeptide or polypeptide fragment separated or substantially free from at least some of the other components of the naturally occurring organism, for example, the cellular components or other polypeptides or nucleic acids commonly found associated with the polypeptide. In representative embodiments of the invention an "isolated" polypeptide, polypeptide fragment and/or protein is at least about 5%, 10%, 15%, 20%, 25%, 30%, 40%, 50%, 60%, 70%, 75%, 80%, 85%, 90%, 95%, 97%, 98%, 99% pure (w/w) or more.

As used herein "nucleic acid" is a macromolecule composed of chains of monomeric nucleotides including, but not limited to deoxyribonucleic acid (DNA) and ribonucleic acid (RNA). A nucleic acid can include a gene. In particular embodiments, the nucleic acids used in the present invention are "isolated" nucleic acids. As used herein, an "isolated" nucleic acid means a nucleic acid separated or substantially free from at least some of the other components of the naturally occurring organism, such as for example, the cell structural components or other polypeptides or nucleic acids commonly found associated with the nucleic acid. In particular embodiments, the "isolated" nucleic acid is at least about 1%, 5%, 10%, 25%, 50%, 60%, 70%, 75%, 80%, 85%, 90%, 95%, 97%, 98%, 99% or more pure (w/w). In other embodiments, an "isolated" nucleic acid indicates that at least about a 5-fold, 10-fold, 25-fold, 100-fold, 1000-fold, 10,000-fold, 100,000-fold or more enrichment of the nucleic acid (w/w) is achieved as compared with the starting material.

As used herein, the term "expression" (and grammatical equivalents) with reference to a nucleic acid refers to transcription of the nucleic acid and, optionally translation.

As used herein, the transitional phrase "consisting essentially of" means that the scope of a claim is to be interpreted to encompass the specified materials or steps recited in the claim" and those that do not materially affect the basic and novel characteristic(s)" of the claimed invention. Thus, the term "consisting essentially of" when used in a claim of this invention is not intended to be interpreted to be equivalent to "comprising."

Various embodiments of the invention are described herein. Any of the features of the various embodiments of the invention described herein can be combined, creating additional embodiments which are intended to be within the scope of the invention.

The sugar cane tissue suitable for the present invention is young tissue. As used herein "young tissue" refers to tissue that has been placed on media for the initiation of callus formation for less than 28 days, as described below. Thus, young tissue of the present invention includes without limitation, tissue that is competent for callus production, micro-callus tissue (i.e., very small early stage callus development), and callus.

Accordingly, in some embodiments of the invention, the sugar cane tissue and/or a cell thereof is less than about 1 day post-initiation (i.e., on the day the sugar cane tissue is initiated into the tissue culture environment and/or placed on the callus inducing media)), less than about 2 days post-initiation, less than about 3 days post-initiation, less than about 4 days post-initiation, less than about 5 days post-initiation, less than about 6 days post-initiation, less than about 7 days post-initiation, less than about 8 days post-initiation, less than about 9 days post-initiation, less than about 10 days post-initiation, less than about 11 days post-initiation, less than about 12 days post-initiation, less than about 13 days post-initiation, less than about 14 days post-initiation, less than about 15 days post-initiation, less than about 16 days post-initiation, less than about 17 days post-initiation, less than about 18 days post-initiation, less than about 19 days post-initiation, less than about 20 days post-initiation, less than about 21 days post-initiation, less than about 22 days post-initiation, less than about 23 days post-initiation, less than about 24 days post-initiation, less than about 25 days post-initiation, less than about 26 days post-initiation, less than about 27 days post-initiation, less than 28 days post-initiation, and the like. Thus, in some particular embodiments of the present invention, the sugar cane tissue and or/cell thereof is less than about 21 days post-initiation. In other embodiments, the sugar cane tissue and or/cell thereof is about less than 1 day post-initiation (e.g., 0 min (e.g., immediately after preparation for initiation), 15 min, 30 min, 45 min, 1 hr, 2 hrs, 3 hrs, 4 hrs, 5 hrs, 6 hrs, 7, hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, and the like), 1, 2, 3, 4, 5, 6, 7, 8, 9, 10, 11, 12, 13, 14, 15, 16, 17, 18, 19, 20, 21, 22, 23, 24, 25, 26, 27, or 28 days post-initiation.

In still other embodiments, the sugar cane tissue and/or cell thereof is in a range from about 0 days to 28 days post-initiation. In other embodiments, the sugar cane tissue and/or cell thereof is in a range from about 0 days to about 25 days post-initiation; from about 0 days to about 23 days post-initiation; from about 0 days to about 21 days post-initiation; from about 0 days to about 20 days post-initiation; from about 0 days to about 19 days post-initiation; from about 0 days to about 18 days post-initiation; from about 0 days to about 16 days post-initiation; from about 0 days to about 14 days post-initiation; from about 0 days to about 12 days post-initiation; from about 0 days to about 10 days post-initiation; from about 0 days to about 9 days post-initiation; from about 0 days to about 8 days post-initiation; from about 0 days to about 7 days post-initiation; from about 0 days to about 6 days post-initiation; from about 0 days to about 5 days post-initiation; from about 0 days to about 4 days post-initiation; from about 0 days to about 3 days post-initiation; from about 0 days to about 2 days post-initiation; from about 1 day to about 28 days post-initiation; from about 1 day to about 25 days post-initiation; from about 1 day to about 23 days post-initiation; from about 1 day to about 21 days post-initiation; from about 1 day to about 20 days post-initiation; from about 1 day to about 19 days post-initiation; from about 1 day to about 18 days post-initiation; from about 1 day to about 16 days post-initiation; from about 1 day to about 14 days post-initiation; from about 1 day to about 12 days post-initiation; from about 1 day to about 10 days post-initiation; from about 1 day to about 9 days post-initiation; from about 1 day to about 8 days post-initiation; from about 1 day to about 7 days post-initiation; from about 1 day to about 6 days post-initiation; from about 1 day to about 5 days post-initiation; from about 1 day to about 4 days post-initiation; from about 1 day to about 3 days post-initiation; from about 2 days to about 28 days post-initiation; from about 2 days to about 26 days post-initiation; from about 2 days to about 24 days post-initiation; from about 2 days to about 22 days post-initiation; from about 2 days to about 20 days post-initiation; from about 2 days to about 19 days post-initiation; from about 2 days to about 18 days post-initiation; from about 2 days to about 17 days post-initiation; from about 2 days to about 16 days post-initiation; from about 2 days to about 14 days post-initiation; from about 2 days to about 12 days post-initiation; from about 2 days to about 10 days post-initiation; from about 2 days to about 9 days post-initiation; from about 2 days to about 8 days post-initiation; from about 2 days to about 7 days post-initiation; from about 2 days to about 6 days post-initiation; from about 2 days to about 5 days post-initiation; from about 2 days to about 4 days post-initiation; from about 3 days to about 28 days post-initiation from about 3 days to about 26 days post-initiation; from about 3 days to about 24 days post-initiation; from about 3 days to about 22 days post-initiation; from about 3 days to about 20 days post-initiation; from about 3 days to about 19 days post-initiation; from about 3 days to about 18 days post-initiation; from about 3 days to about 17 days post-initiation; from about 3 days to about 16 days post-initiation; from about 3 days to about 14 days post-initiation; from about 3 days to about 12 days post-initiation; from about 3 days to about 10 days post-initiation; from about 3 days to about 9 days post-initiation; from about 3 days to about 8 days post-initiation; from about 3 days to about 7 days post-initiation; from about 3 day to about 6 days post-initiation; from about 3 days to about 5 days post-initiation; from about 4 days to about 28 days post-initiation; from about 4 days to about 26 days post-initiation; from about 4 days to about 24 days post-initiation; from about 4 days to about 22 days post-initiation; from about 4 days to about 20 days post-initiation; from about 4 days to about 19 days post-initiation; from about 4 days to about 18 days post-initiation; from about 4 days to about 17 days post-initiation; from about 4 days to about 16 days post-initiation; from about 4 days to about 14 days post-initiation; from about 4 days to about 12 days post-initiation; from about 4 days to about 10 days post-initiation; from about 4 days to about 9 days post-initiation; from about 4 days to about 8 days post-initiation; from about 4 days to about 7 days post-initiation; from about 4 days to about 6 days post-initiation; from about 5 days to about 28 days post-initiation; from about 5 days to about 25 days post-initiation; from about 5 days to about 23 days post-initiation; from about 5 days to about 21 days post-initiation; from about 5 days to about 20 days post-initiation; from about 5 days to about 19 days post-initiation; from about 5 days to about 18 days post-initiation; from about 5 days to about 17 days post-initiation; from about 5 days to about 15 days post-initiation; from about 5 days to about 14 days post-initiation; from about 5 days to about 12 days post-initiation; from about 5 days to about 10 days post-initiation; from about 5 days to about 9 days post-initiation; from about 5 days to about 8 days post-initiation; from about 5 days to about 7 days post-initiation; from about 6 days to about 28 days post-initiation from about 6 days to about 26 days post-initiation; from about 6 days to about 24 days post-initiation; from about 6 days to about 22 days post-initiation; from about 6 days to about 20 days post-initiation; from about 6 days to about 19 days post-initiation; from about 6 days to about 18 days post-initiation; from about 6 days to about 17 days post-initiation; from about 6 days to about 16 days post-initiation; from about 6 days to about 14 days post-initiation; from about 6 days to about 12 days post-initiation; from about 6 days to about 10 days post-initiation; from about 6 days to about 9 days post-initiation; from about 6 days to about 8 days post-initiation; from about 8 days to about 28 days post-initiation from about 8 days to about 26 days post-initiation; from about 8 days to about 24 days post-initiation; from about 6 days to about 22 days post-initiation; from about 6 days to about 20 days post-initiation; from about 6 days to about 19 days post-initiation; from about 8 days to about 18 days post-initiation; from about 8 days to about 17 days post-initiation; from about 8 days to about 16 days post-initiation; from about 8 days to about 14 days post-initiation; from about 8 days to about 12 days post-initiation; from about 8 days to about 10 days post-initiation; from about 10 days to about 28 days post-initiation; from about 10 days to about 26 days post-initiation; from about 10 days to about 24 days post-initiation; from about 10 days to about 22 days post-initiation; from about 10 days to about 20 days post-initiation; from about 10 days to about 19 days post-initiation; from about 10 days to about 18 days post-initiation; from about 10 days to about 17 days post-initiation; from about 10 days to about 15 days post-initiation; from about 10 days to about 12 days post-initiation; from about 12 days to about 28 days post-initiation; from about 12 days to about 26 days post-initiation; from about 12 days to about 24 days post-initiation; from about 12 days to about 22 days post-initiation; from about 12 days to about 20 days post-initiation; from about 12 days to about 18 days post-initiation; from about 12 days to about 16 days post-initiation; from about 12 days to about 14 days post-initiation; from about 14 days to about 28 days post-initiation; from about 14 days to about 26 days post-initiation; from about 14 days to about 24 days post-initiation; from about 14 days to about 22 days post-initiation; from about 14 days to about 21 days post-initiation; from about 14 days to about 20 days post-initiation; from about 14 days to about 18 days post-initiation; from about 14 days to about 16 days post-initiation; from about 16 days to about 28 days post-initiation; from about 16 days to about 26 days post-initiation; from about 16 days to about 24 days post-initiation; from about 16 days to about 22 days post-initiation; from about 16 days to about 20 days post-initiation; from about 16 days to about 19 days post-initiation; from about 16 days to about 18 days post-initiation; from about 18 days to about 28 days post-initiation; from about 18 days to about 26 days post-initiation; from about 18 days to about 24 days post-initiation; from about 18 days to about 22 days post-initiation; from about 18 days to about 20 days post-initiation; from about 20 days to about 28 days post-initiation; from about 20 days to about 26 days post-initiation; from about 20 days to about 24 days post-initiation; from about 20 days to about 22 days post-initiation; from about 22 days to about 28 days post-initiation; from about 22 days to about 26 days post-initiation; from about 22 days to about 24 days post-initiation; from about 24 days to about 28 days post-initiation; from about 24 days to about 26 days post-initiation; from about 26 days to about 28 days post-initiation; and the like. In some particular embodiments, the sugar cane tissue and or/cell thereof is from about 14 days to about 21 days post-initiation. In other embodiments, the sugar cane tissue and or/cell thereof is from about 6 days to about 14 days post initiation. In further embodiments, the sugar cane tissue and or/cell thereof is from about 6 days to about 23 days post initiation. In still further embodiments, the sugar cane tissue and or/cell thereof is from about 1 day to about 14 days post initiation.

As used herein "days post-initiation" means the number of days since the plant tissue was initiated into tissue culture and/or placed onto media for inducing embryogenic callus formation. Thus, as an example, the day after the plant tissue was placed onto the embryogenic induction media is one day post-initiation.

Culture conditions sufficient for induction of embryogenic callus formation are known to those skilled in the art, and may vary according to the sugar cane cultivar. Thus, for example, suitable media for establishment and maintenance of embryogenic cultures are described in, e. g. Wang, ed. Methods in Molecular Biology Vol. 344, page 227-235; Published International Application No. WO 01/33943; U.S. Pat. No. 5,908,771; U.S. Pat. No. 6,242,257; Croy, R. R. D. (Ed.) *Plant Molecular Biology Labfax*, Bios Scientific Publishers Ltd. (1993); and Jones, H. (Ed.) *Plant Transfer and Expression Protocols*, Humana Press (1995), and in the references cited therein. Each of these references is incorporated herein by reference in their entirety.

The culture medium may include Murashige & Skoog (MS) nutrient formulation (Murashige & Skoog, 1962, *Physiologia Plantarum* 15 473) or Gamborg's medium (Gamborg et al., 1968, *Exp. Cell Res* 50:151-158) or any number of additional media formulations available or developed for the tissue culture of sugar cane. In some embodiments, the medium comprises MS formulation. It will be appreciated that the above mentioned media are commercially available, as are other potentially useful media. The medium may further comprise sucrose, and may additionally include agar. Thus, it will be appreciated that the plant tissue may be cultured in solid or liquid medium.

Additional components of the medium can include phytohormones such as cytokinin and/or auxin. In various embodiments, the cytokinin and/or cytokinin-like compounds include, but are not limited to, kinetin, TDZ, $N_6$-benzyladenine (BA), zeatin, α-isopentyladenosine, diphenylurea, and the like, and any combination thereof.

In some embodiments, the auxin and/or auxin-like compounds include, but are not limited to, 1-napthaleneacetic acid (NAA), 2,4 dichlorophenoxyacetic acid (2,4D), dicamba, indole-3-butyric acid (IBA), p-chlorophenoxyacetic acid (CPA), indole-3-acetic acid (IAA), 2,4,5-trichlorophenoxyacetic acid, phenylacetic acid, picloram, β-napthoxyacetic acid, dicamba, trans-cinnamic acid, and the like, and any combination thereof.

It will be readily apparent to the skilled artisan that the most efficacious concentrations of auxin and/or cytokinin can be determined empirically by cross-testing various concentrations of auxin and cytokinin. The optimal concentration of either or both can be tailored according to the particular plant cultivar from which the sugar cane tissue was derived.

The sugar cane tissue then can be subjected to inoculation, as described herein, wherein the sugar tissue or cell thereof is contacted with an inoculation culture comprising *Agrobacteria* (or any other bacterial strain competent for transfer of nucleic acids), that comprise a nucleotide sequence of interest that is to be introduced into the sugar cane tissue.

In some embodiments, a sugar cane tissue for use in the *Agrobacterium*-mediated transformation methods of the invention means the organs (e.g., leaves, stems, roots, etc.), seeds, cells, and progeny of the same, of the sugar cane plant. Thus, plant, plant part, plant tissue also includes, without limitation, protoplasts, nodules, callus (e.g., embryogenic callus tissue), suspension culture, embryos, as well as flowers, ovules, stems, fruits, leaves, primary stalks, side shoots (also referred to as tillers), roots, root tips and the like originating in plants or their progeny. Sugar cane plant cell includes, without limitation, a cell obtained from a seed, embryo, meristematic region, callus tissue, suspension culture, leaf, root, shoot, gametophyte, sporophyte, pollen and/or microspore. The sugar cane tissue of the present invention can be derived from greenhouse grown plants or from field grown plants.

In some embodiments, suitable plant tissue for use in the *Agrobacterium*-mediated transformation methods of the invention may be any sugar cane-derived tissue or cell thereof. In other embodiments, the plant tissue for use in the *Agrobacterium*-mediated transformation methods of the invention may be any sugar cane-derived tissue or cell thereof that is amenable to regeneration of a whole plant following introduction of the nucleic acid of interest (e.g., embryogenic callus). Thus, in some particular embodiments, the sugar cane tissue can be callus tissue (e.g., embryogenic callus tissue). As used herein, "embryogenic callus" means tissues or cells that are undifferentiated and without significant structure but with the potential to form a more differentiated tissue (e.g., embryogenic tissue) that can produce embryos and germinate into plants.

Exemplary tissues include, but are not limited to, young leaf bases, immature flowers or inflorescences, axillary buds, isolated shoot or root meristems, immature leaf rolls, immature side shoots (also referred to as immature tillers), primary stalks/shoots, seeds, isolated embryos, and the like, and any combination thereof.

Exemplary sugar cane tissue includes, but is not limited to, tissue derived from young leaf bases, immature flowers or inflorescences, axillary buds, isolated shoot or root meristems, immature leaf whorls/rolls, immature side shoots (also referred to as immature tillers or suckers), seeds, isolated embryos and the like. In some embodiments, the sugar cane tissue can be immature leaf whorls excised from either a primary stalk or from a tiller of a sugar cane plant. In some embodiments, the sugar cane tissue is embryogenic callus tissue derived from the foregoing tissues. In other embodiments, the sugar cane tissue is embryogenic callus derived from young sugar cane tiller tissue (e.g., immature side shoots). In still other embodiments, the sugar cane tissue is obtained from a leaf roll segment or a leaf sheath segment excised from a tiller. In additional embodiments, the sugar cane tissue is embryogenic callus tissue derived from a leaf roll segment or a leaf sheath segment excised from a tiller. In further embodiments, the sugar cane tissue is embryogenic callus derived from immature leaf whorl tissue. Embryogenic callus is derived from the aforementioned plant tissues via methods of pre-culturing as known in the art and described below.

As described above, in some embodiments, the sugar cane tissue can be derived from primary or side shoots. The age of the primary or side shoot at this stage is typically between about one and six months old, including about one to about three months, about one to about four months, about one to about five months, about two to about three months, or about two to about four months old. In other embodiments, the age of the side shoot at this stage is between six months and 12 months old. In some embodiments, side shoots can be obtained from greenhouse-grown plants. In other embodiments, the plant tissues used with the present invention are derived from field grown plants.

Primary and side shoots can be excised from the plant and sterilized by standard methods as described herein and well known to one of skill in the art to establish sterile cultures in an artificial medium. For example, the side shoots can be contacted with a 70% ethanol solution, or a 20% bleach solution. Following sterilization of the excised shoot, a immature leaf whorl, segment, slice, or section of plant tissue is obtained. In some embodiments, the section may be from about 0.1 mm to about 100 mm in thickness. Thus, in some embodiments, the section may be about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.5 mm, about 2 mm, about 3 mm, about 4 mm, about 5 mm, about 6 mm, 7 mm, about 8 mm, about 9 mm, about 10 mm, about 12 mm, about 14 mm, about 16 mm, about 18 mm, about 20 mm, about 25 mm, about 30 mm, about 35 mm, about 40 mm, about 45 mm, about 50 mm, about 55 mm, 60 mm, about 65 mm, about 70 mm, about 75 mm, about 80 mm, about 85 mm, about 90 mm, about 95 mm or 100 mm in thickness. The plant tissue obtained in this way is often referred to as an "explant." The term "explant" refers to living tissue removed from an organism and placed in an axenic environment for further tissue culture.

In some embodiments, the explant may be obtained from primary or side shoot tissues including leaf spindle or whorl, stems, leaf sheath, leaf roll (meristematic region), node, or internode segments. In some embodiments, the explant can be leaf sheath or leaf roll sections. The segment may be cut from just above the apical meristem up to about 0.1 mm to about 100 mm above the apical meristem. Thus, in some embodiments, the segment may be cut from just above the apical meristem up to about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.5 mm, about 2 mm, about 3 mm, about 4 mm, about 5 mm, about 6 mm, 7 mm, about 8 mm, about 9 mm, about 10 mm, about 12 mm, about 14 mm, about 16 mm, about 18 mm, about 20 mm, about 25 mm, about 30 mm, about 35 mm, about 40 mm, about 45 mm, about 50 mm, about 55 mm, 60 mm, about 65 mm, about 70 mm, about 75 mm, about 80 mm, about 85 mm, about 90 mm, about 95 mm or 100 mm above the apical meristem. In various embodiments, the explant is not a node segment or is not an internode segment. As used herein, "node segment" means any joint in a stem from which one or more leaves may grow and also includes any lateral (axillary) buds on the side of the stem, as in a leaf axil. The part of the stem between two nodes is termed the "internode." The outer one or two leaves may be removed from the side shoot prior to segmenting.

"Introducing" in the context of a nucleotide sequence of interest means presenting to the plant the nucleotide sequence in such a manner that the nucleotide sequence gains access to the interior of a cell of the sugar cane plant. Where more than one nucleotide sequence is to be introduced, these nucleotide sequences can be assembled as part of a single polynucleotide or nucleic acid construct, or as separate polynucleotide or nucleic acid constructs, and can be located on the same or different transformation vectors. Further, these polynucleotides can be introduced into sugar cane plant cells in a single transformation event, in separate transformation events, or, e.g., as part of a breeding protocol.

"Transient transformation" in the context of a nucleic acid means that a nucleic acid is introduced into the cell and does not integrate into the genome of the cell.

By "stably introducing" or "stably introduced" in the context of a nucleic acid introduced into a cell is intended that the introduced nucleic acid is stably incorporated into the genome of the cell, and thus the cell is stably transformed with the nucleic acid.

"Stable transformation" or "stably transformed" as used herein means that a nucleic acid that is introduced into a cell and integrates into the genome of the cell. As such, the integrated nucleic acid is capable of being inherited by the progeny thereof, more particularly, by the progeny of multiple successive generations. The genome as used herein also includes the plastid genome, and therefore includes integration of the nucleic acid into, for example, the chloroplast genome. Stable transformation as used herein can also refer to a transgene that is maintained extrachromosomally, for example, as a minichromosome.

Thus, in some embodiments, the sugar cane tissue and/or cell thereof is transiently transformed. In other embodiments, the sugar cane tissue and/or cell thereof is stably transformed. Thus, in some embodiments wherein the sugar cane tissue and/or cell thereof is stably transformed, a stably transformed sugar cane plant can be regenerated.

In accordance with the methods of the present invention, a nucleotide sequence of interest is introduced into a bacterial strain competent for nucleic acid transfer (e.g., an *Agrobacterium* strain) via conventional transformation methods, and the bactrial strain is then utilized in the transformation methods of the invention to introduce the nucleotide sequences of interest into a sugar cane plant or plant part thereof. As an example, many vectors are available for transformation of *Agrobacterium*. These typically carry at least one T-DNA border sequence and include vectors such as pBIN19 (Bevan, *Nucleic Acids Res.* 12:8711-8721 (1984)). For the construction of vectors useful in *Agrobacterium* transformation, see, for example, U.S. Patent Application Publication No. 2006/0260011, herein incorporated by reference in its entirety.

Thus, *Agrobacterium* transformation typically involves the transfer of a binary vector carrying the foreign nucleotide sequence of interest to an appropriate *Agrobacterium* strain which may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a tri-parental mating procedure using *E. coli* carrying the recombinant binary vector, a helper *E. coli* strain that carries a plasmid and which is able to mobilize the recombinant binary vector to the target *Agrobacterium* strain. Alternatively, the recombinant binary vector can be transferred to *Agrobacterium* by DNA transformation (Hofgen and Willmitzer (1988) *Nucleic Acids Res.* 16:9877).

Thus, in some embodiments, the bacterium competent for nucleic acid transfer can be *Agrobacterium*. In particular embodiments, the *Agrobacterium* is *Agrobacterium tumefaciens*. Methods of *Agrobacterium*-mediated transformation of plants are generally known in the art. See, U.S. Pat. Nos. 5,563,055 and 5,981,840; see also, WO 94/00977 and U.S. Pat. No. 5,591,616, See also, Negrotto et al., Plant Cell Reports 19: 798-803 (2000), Arencibia et al. (1998) *Transgenic Res.* 7:123-222; Arencibia & Carmona "Sugar cane (*Saccharum* spp.)," in *Methods in Molecular Biology, Agrobacterium Protocols*, Vol. 2, ed. Wang ($2^{nd}$ ed., Humana Press, Inc.), pages 227-235 (2007); de la Riva et al. (1998) *Electron. J. Biotechnol.* 1:118-133; Manickavasagam et al. (2004) *Plant Cell Rep.* 23:134-143; Opabode (2006) *Biotechnol. Mol. Biol. Rev,* 1:12-20; and Zhang et al. (2006) *J. Integr. Plant Biol.* 48:453-459) all of which are incorporated herein by reference.

As used herein, "*Agrobacterium*" means a species, sub-species, or strain of *Agrobacterium* that is able to mobilize and selectively transfer T-DNA into a plant or plant cell thereof. Thus, in some embodiments, the bacterium competent for nucleic acid transfer can be *Agrobacterium*. In particular embodiments of the invention, *Agrobacterium* can be *Agrobacterium rhizogenes* (i.e., *Rhizobium rhizogenes*) or *A. tumefaciens*. Any strain of *Agrobacterium* capable of mobilizing and selectively transferring T-DNA into a plant or plant cell can be used in the present invention. In some embodiments, wild-type strains are used. In other embodiments, "disarmed" derivatives of *Agrobacterium* species, in which the tumor-inducing sequences of the Ti plasmid have been removed, are used. Examples of suitable *A. tumefaciens* strains include, but are not limited to, e.g., EHA101, as described by Hood et al. (1986) *J. Bacteriol.* 168:1291-1301); LBA4404, as described by Hoekema et al. (1983) *Nature* 303:179-180; and C58 (pMP90), as described by Koncz and Schell (1986) *Mol. Gen. Genet.* 204:383-396, EHA 105, AGLI and AGL0, and the like, and any combination thereof. Examples of suitable *Agrobacterium rhizogenes* strains include, but are not limited to, 15834, as described by Birot et al. (Biochem, 25: 323-35) and R1000.

In further embodiments, in addition to *Agrobacterium* species and strains, other bacterial species and strains thereof, which are competent for nucleic acid transfer can be used in the methods of transformation of the present invention (see, for example those described by CAMBIA (www-.cambia.org); see also Broothaerts et al. *Nature* 433:629-633 (2005)). Non-limiting examples of non-*Agrobacterium* bacteria competent for nucleic acid transfer include *Sinorhizobium, Mesorhizobium* and *Rhizobium* (Id.).

Any suitable method for inoculating the sugar cane tissue and/or cell thereof to obtain an *Agrobacterium*-inoculated plant tissue or cell thereof can be used in the methods of the present invention, including those described herein and those known to one of skill in the art. In some embodiments, inoculation involves mixing the sugar cane tissue and/or cell thereof with an inoculation culture that comprises an *Agrobacterium* strain that harbors a plasmid or vector comprising a nucleotide sequence of interest. Numerous transformation vectors available for plant transformation are known in to those of ordinary skill in the plant transformation arts, and the nucleic acids useful to this invention can be used in conjunction with any such vectors.

Thus, in some embodiments, an inoculation culture is an inoculation suspension that has been prepared from cultured bacteria (e.g., *Agrobacterium*). In this manner, the bacterium strain harboring the nucleotide sequence of interest to be transformed into the sugar cane plant material is cultured on an appropriate culture medium supplemented with antibiotics selective for the strain and vector (see, for example, the protocol described in the Experimental section herein below). Those of skill in the art are familiar with procedures for growth of bacteria, for example, *Agrobacterium*, and suitable culture conditions. Typically an *Agrobacterium* culture is inoculated from a glycerol stock or streaked plate and is grown overnight. The bacterial cells are then washed and resuspended in a culture medium suitable for inoculation of the sugar cane tissue. As used herein "inoculation suspension" means a suspension of bacterial cells (e.g., *Agrobacterium* spp.) to be used for inoculating plant material. "Inoculation culture" refers to the combination of the bacterial cells with the plant material.

Inoculation (i.e., infection) itself can be for at least about one minute to about twelve hours (e.g., overnight) at about room temperature (e.g., at about 20° C. to about 25° C.). During inoculation, it is contemplated that various additional treatments can be applied to aid with *Agrobacterium* infection such as sonication or vacuum infiltration of the inoculation culture. For example, the inoculation culture can be sonicated as described in Trick and Finer (*Plant Cell Rep.* 17:482-488 (1998)) and U.S. Pat. No. 5,693,512. Alternatively, or in addition, the inoculation culture can be vacuum infiltrated as described in Amoah et al. *J. Exp. Bot.* 52:1135-1142 (2001) and Park et al. *Plant Cell Rep.* 24:494-500 (2005)).

In some embodiments, it is contemplated that the sugar cane tissue is subjected to a temperature differential pretreatment prior to inoculation. By "temperature differential pretreatment" is intended the sugar cane tissue is exposed to a temperature, higher than the temperature at which inoculation will be carried out. Thus, for example, where inoculation is to be carried out at about room temperature (e.g., about 20° C. to about 25° C.), the temperature differential pretreatment can comprise exposure of the sugar cane tissue to a temperature that is about 5° C., about 10° C., about 15° C., about 20° C., about 25° C., or about 30° C. higher (in which case the sugar cane tissue is exposed to a heat pretreatment; ie., heat shock) than the temperature at which inoculation will be carried out (for example, room temperature). The length of the temperature differential pretreatment will vary depending upon the type and source of the sugar cane tissue. Thus, in some embodiments, the length of the temperature differential pretreatment is about 1 minute to about 60 minutes, 1 minute to about 50 minutes, 1 minute to about 40 minutes, 1 minute to about 30 minutes, about 1 minute to about 20 minutes, about 1 minute to about 15 minutes, about 1 minute to about 10 minutes, or about 1 minute to about 5 minutes. In other embodiments, the length of the temperature differential pretreatment is 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, 60 min, and the like.

Thus, in some embodiments, it is contemplated that the sugar cane tissue is pretreated with a heat shock prior to inoculation using methods known to those of skill in the art. Thus, as a non-limiting example, heat shock comprises contacting the plant tissue with medium such as basic medium (e.g., Murashige and Skoog medium; Murashige and Skoog (1962) *Physiol. Plant* 15:473-497) warmed to a temperature of about 35° C. to about 55° C., for about 1 minute to about 15 minutes. In another non-limiting example, heat shock comprises contacting the plant tissue with media at a temperature of about 45° C. for about 5 minutes.

As used herein, "co-culture medium" or "co-cultivating medium" and the like, means any medium known in the art for culturing plant tissues after inoculation with *Agrobacterium*. The constituents of co-cultivation media are generally known in the art, and include the sugar cane co-culture medium referred to herein as SCCoCult.

By "co-cultivation" and "co-cultivating" is intended the time period of culture following inoculation of the plant tissue (e.g., contacting the plant tissue with an *Agrobacterium* strain or other bacteria capable of nucleic acid transfer) up until the time period when the bacteria are removed, inactivated or suppressed. Thus, for example, co-cultivating" can refer to the time period of culture following inoculation of the plant tissue up until the time period when the growth and metabolic activity of the bacteria within the inoculated tissue is suppressed by the addition of compounds (e.g., bacteriocidal or bacteriostatic agents) or through processes that inhibit the growth of the bacteria or a combination thereof. As used herein, "suppress," "suppressed," "suppression," (and grammatical variations thereof) means that the activity (e.g., *Agrobacterium* growth and reproduction) is slowed or halted due to the addition of an agent (e.g., inhibitor, antibiotic, and the like) and/or a change in the culture (growing) conditions (e.g., media, temperature, humidity, light, and the like) as compared to the activity in the absence of the agent or change. Usually the co-cultivation process ends at the start of a resting, selection or regeneration step.

In some embodiments, a method of transforming a sugar cane tissue and/or cell thereof is provided, the method comprising: a) inoculating the sugar cane tissue or cell thereof that is less than 28 days post-initiation with *Agrobacterium*, said *Agrobacterium* comprising a nucleotide sequence of interest, to obtain an *Agrobacterium*-inoculated sugar cane tissue or cell thereof; b) co-cultivating said *Agrobacterium*-inoculated sugar cane tissue or cell thereof on a surface in a desiccating environment (i.e., in the absence of culture media) for a time period sufficient to reduce original weight of said *Agrobacterium*-inoculated sugar cane tissue or cell thereof; and optionally c) selecting a transformed sugar cane tissue or cell thereof comprising said nucleotide sequence of interest. In some embodiments, the sugar cane tissue or cell thereof is in a range from about 0 days to 28 days post-initiation, from about 14 days to about 21 days post-initiation, and the like as described above. Thus, in some embodiments of the invention the co-cultivating can optionally occur in a desiccating environment.

As used herein, "desiccating environment" means that the co-cultivation step is performed in the absence of semi-solid or liquid co-culture medium thereby allowing the plant tissue being co-cultivated with the *Agrobacterium* to dry, and thus be reduced in its original weight as described below. In other embodiments, "desiccating environment" means co-cultivating the *Agrobacterium*-inoculated plant tissue on a surface without (i.e., in the absence of) co-cultivating media or other added liquid for a time period sufficient to reduce the original weight of the *Agrobacterium*-inoculated plant tissue.

In other embodiments of the invention, the *Agrobacterium*-inoculated tissue thereof is subjected to a co-cultivation step that includes culturing the inoculated plant tissue on a surface in an extreme desiccating environment for a time period sufficient to reduce the original weight of the inoculated plant tissue. As used herein, the term "extreme desiccating environment" means excess inoculation suspension is substantially removed prior to the co-cultivation step wherein the tissue is co-cultivated with *Agrobacterium* in the absence of co-cultivation media. In other embodiments, pre-cultivation media is substantially removed prior to the co-cultivation step wherein the tissue is co-cultivated with *Agrobacterium* in the absence of co-cultivation media. Thus, it is recognized that the plant tissue when removed from the inoculation suspension (e.g., a bacterial suspension culture) may retain residual inoculation suspension adhering thereto or the plant tissue when removed from the pre-culture media (e.g., media for the initiation of callus) may retain residual pre-culture media adhering thereto.

Therefore, to maximize the desiccating environment of the surface (i.e., create an extreme desiccating environment) that will support the inoculated plant tissue during the co-cultivation step, residual or excess inoculation suspension and/or pre-culture media can be substantially removed from the plant tissue. By "substantially removed" is intended a de minimus or reduced amount of inoculation suspension and/or pre-culture media may be present on (i.e., adhered to) the inoculated plant tissue when it is placed on a surface in a desiccating environment so long as the amount that remains does not counter the objective of the desiccating or extreme desiccating environment (e.g., to reduce the original weight of the inoculated plant tissue as described below). Thus, in some embodiments of the invention the co-cultivating can optionally occur in an extreme desiccating environment.

Thus, in some embodiments, the *Agrobacterium*-inoculated tissue thereof is subjected to pre-drying which comprises substantially removing inoculation suspension from said *Agrobacterium*-inoculated sugar cane tissue prior to co-cultivating in the absence of co-cultivation media. It is noted that the sugar cane tissue can be subjected to pre-drying prior to inoculation in embodiments in which the co-cultivation is in a desiccating or extreme desiccating environment and in those embodiments in which the co-cultivation does not occur in a desiccating or extreme desiccating environment.

Any method that substantially removes the *Agrobacterium*-containing inoculation suspension can be used to pre-dry the plant tissue prior to the co-cultivation step. Non-limiting examples of methods for pre-drying include draining, blotting on dry sterile absorbent paper (e.g., filter paper), air drying the inoculated plant tissue, or any combination thereof; prior to the co-cultivation step. Where air drying is used, the inoculated plant tissue can be air dried, for example, under a laminar hood or other means for evaporation, for about 1 minute to about 60 minutes, for example, about 1 minute, about 5 minutes, about 10 minutes, about 15 minutes, about 30 minutes, about 60 minutes, or any time period between about 1 minute and about 60 minutes prior to the co-cultivation step. When blotting with paper, the inoculated plant tissue can be blotted sequentially with multiple sterile papers until the paper shows no signs of wetness or is substantially dry (i.e., a visual inspection of the filter paper immediately after blotting the inoculated plant tissue does not identify any moisture or damp spots on the paper). The *Agrobacterium*-inoculated plant tissue then can be co-cultivated on a surface in a desiccating environment.

In additional embodiments, the term "extreme desiccating environment" means co-cultivating the *Agrobacterium*-inoculated plant tissue a surface comprising at least one dry, absorbent paper (e.g., filter paper), wherein the dry paper is changed periodically throughout the co-cultivation. "Periodically," as used herein, means, for example, hourly, daily, every two days, every three days, and the like. Thus, in some embodiments, the co-cultivating comprises culturing said *Agrobacterium*-inoculated sugar cane tissue on at least one layer of dry paper, wherein the dry paper is changed daily during co-cultivation.

In some particular embodiments, the plant tissue is pre-dried as described above, and the *Agrobacterium*-inoculated plant tissue is o-cultivated a surface comprising at least one dry, absorbent paper, wherein the dry paper is changed periodically throughout the co-cultivation the co-cultivation Accordingly, in some embodiments of the present invention, the inoculated tissue thereof is co-cultivated on a surface in a desiccating environment and/or an extreme desiccating environment for a time period sufficient to reduce the original weight of the inoculated plant tissue by less than 1%, by about 1%, about 5%, about 10%, about 15%, about 20%, about 25% about 30%, about 35%, about 40%, about 45%, about 50%, about 55%, about 60%, about 65%, about 70%, about 75%, about 80%, and the like. In other embodiments, the original weight is reduced by more than about 35% up to about 60%, for example, about 36%, 37%, 38%, 39%, 40%, 41%, 42%, 43%, 44%, 45%, 46%, 47%, 48% 49%, 50%, 51%, 52%, 53%, 54%, 55%, 56%, 57%, 58%, 59%, 60%, and other such values between about 35% and about 60%. In some embodiments, the original weight is reduced by less than 1% to about 10%, by more than about 1% to about 10%, about 1% to about 15%, about 1% to about 19%, about 1% to about 20%, about 1% to about 25%, about 1% to about 30%, about 1% to about 40%, about 1% to about 50%, about 1% to about 55%, about 1% to about 60%, about 1% to about 70%, about 1% to about 80%, about 10% to about 20%, about 10% to about 25%, about 10% to about 30%, about 10% to about 40%, about 10% to about 50%, about 10% to about 60%, about 10% to about 70%, about 10% to about 80%, about 15% to about 25%, about 15% to about 30%, about 15% to about 40%, about 15% to about 50%, about 15% to about 60%, about 15% to about 70%, about 15% to about 80%, about 20% to about 30%, about 20% to about 40%, about 20% to about 50%, about 20% to about 60%, about 20% to about 70%, about 20% to about 75%, about 20% to about 80%, about 30% to about 40%, about 30% to about 50%, about 30% to about 60%, about 30% to about 65%, about 30% to about 70%, about 30% to about 80%, about 40% to about 50%, about 40% to about 60%, about 40% to about 70%, about 40% to about 80%, about 50% to about 60%, about 50% to about 65%, about 50% to about 70%, about 50% to about 75%, about 50% to about 80%, about 60% to about 65%, about 60% to about 70%, about 60% to about 75%, about 60% to about 80%, about 65% to about 70%, about 65% to about 80%, about 75% to about 80%, and the like and other such values between about 1% and about 80%. In some embodiments, the original weight is reduced by more than about 1% to about 13%, by more than about 1% to about 19%, by more than about 36% to about 50%.

In further embodiments, the inoculated tissue is co-cultivated on a surface in a desiccating and/or extreme desiccating environment for a time period sufficient to reduce the original weight of the inoculated plant tissue by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, and the like. Thus, in some embodiments, the original weight is reduced by at least about 35%. In additional embodiments, the original weight is reduced by at least about 55%.

Accordingly, in some embodiments, the original weight of said *Agrobacterium*-inoculated sugar cane tissue is reduced by more than about 1% to about 55%. In still further embodiments, the original weight of said *Agrobacterium*-inoculated sugar cane tissue is reduced by about 1% to about 10%. In additional embodiments, the original weight of said *Agrobacterium*-inoculated sugar cane tissue is reduced by at least about 35%. In other embodiments, the original weight of said *Agrobacterium*-inoculated sugar cane tissue is reduced by at least about 55%. Thus, for example, where the original weight of the inoculated plant tissue is 20 grams, the time period of the co-cultivation step in the desiccating environment is sufficient to reduce the weight of the inoculated tissue by more than about 35% (i.e, to a weight of less than about 13 grams). Desiccation of the plant tissue during co-cultivation to reduce the original weight of the plant tissue as described herein significantly improves transformation efficiency of sugar cane.

By "original weight" is intended the weight of the *Agrobacterium*-inoculated sugar cane tissue prior to the start of the transformation process. In some embodiments, the transformation process begins with exposing the sugar cane tissue to a temperature shock, as described below. In other embodiments of the invention, the tissue is not exposed to temperature shock and the transformation process begins with the addition of *Agrobacterium* or other appropriate bacterium to the sugar cane tissue. Thus, the "original weight" refers to the weight of the tissue that is determined prior to inoculation. Accordingly, a reduction in original weight as used herein refers to the weight of the plant tissue taken prior to inoculation with an inoculation suspension comprising bacteria competent for nucleic acid transfer (e.g., *Agrobacterium*) as compared to the weight of the tissue determined after co-cultivation with the bacteria. Based on the weight that is determined at these two time points (i.e., prior to inoculation and after co-cultivation), a percentage in reduction of original weight can be determined.

The time period sufficient to reduce the original weight of the *Agrobacterium*-inoculated plant tissue will depend upon the size of the inoculated plant tissue, the type of tissue (for example, callus tissue versus meristematic tissue), and physical parameters associated with the desiccating or extreme desiccating environment. Thus, for example, the environment may be manipulated to accelerate the desiccation of inoculated plant tissue. In some embodiments, the co-cultivation step may be performed in the presence of air flow (e.g., in a laminar hood or near a fan) to accelerate evaporation, in the presence of a vacuum, or in the presence of a suitable desiccant (e.g., calcium oxide, sulfuric acid, silica gel, etc.).

In some embodiments, the co-cultivation time period can be about 1 day to about 14 days, about 2 days to about 14 days, about 2 days to about 12 days, about 2 days to about 10 days, about 2 days to about 8 days, about 2 days to about 6 days, about 2 days to about 4 days, about 3 days to about 14 days, about 3 days to about 12 days, about 3 days to about 10 days, about 3 days to about 8 days about 3 days to about 6 days, about 3 days to about 4 days, about 4 days to about 14 days, about 4 days to about 12 days, about 4 days to about 10 days, about 4 days to about 8 days, about 4 days to about 6 days, about 5 days to about 14 days, about 5 days to about 12 days, about 5 days to about 10 days, about 5 days to about 8 days about 5 days to about 6 days, about 6 days to about 14 days, about 6 days to about 12 days, about 6 days to about 10 days, about 6 days to about 8 days, about 7 days to about 14 days, about 7 days to about 12 days, about 7 days to about 10 days, about 7 days to about 8 days, about 8 days to about 14 days, about 8 days to about 12 days, about 8 days to about 10 days, about 9 days to about 14 days, about 9 days to about 12 days, about 9 days to about 10 days, about 10 days to about 14 days, about 10 days to about 12 days, and the like. In other embodiments, the co-culture period can be for 1 day, 2 days, 3 days, 4 days, 5 days, 6 days, 7 days, 8 days, 9 days, 10 days, 11 days, 12 days, 13 days, or 14 days. In some embodiments, the co-cultivation time period described above can be combined in various embodiments with the changes in original weight of the plant tissue as described above. Thus, any of the co-cultivation time periods can be combined with any of the changes in original weight of the plant tissue as described above, with the young callus of various ages post-initiation as described above and/or with the addition of liquid to the co-cultivation as described above.

The surface on which the co-cultivation step is carried out includes any suitable surface for supporting the *Agrobacterium*-inoculated plant material. In some embodiments, the surface on which the co-cultivation step is carried out includes any suitable surface for supporting the *Agrobacterium*-inoculated plant material as long as this surface is amenable to subjecting the plant material to a desiccating environment.

Exemplary surfaces include, but are not limited to, the surface of a vessel, flask, dish, e.g., a petri or culture dish, a container, and the like. Such vessels can be comprised of any suitable material including, but not limited to, glass, porcelain, plastics (e.g., polystyrene), and the like. Other suitable surfaces suitable for creating a desiccating or extreme desiccating environment include dry absorbent paper (e.g., filter paper (i.e., a porous paper suitable for use as a filter paper (e.g., Whatman® brand filter paper)), seed germination paper, paper towel, blot paper, coffee filter, napkin and the like).

Where paper is the surface, it is recognized that one or more layers of the paper may be utilized to facilitate the desiccation of the inoculated plant material, for example, by acting as an absorption wick. Thus, for example, in some embodiments, the surface used during the co-cultivation step comprises, consists essentially of and/or consists of at least one layer of a dry filter paper. In other embodiments, the surface used during the co-cultivation step comprises, consists essentially of and/or consists of two layers of a dry filter paper or three layers of a dry filter paper. In other embodiments, the surface used during the co-cultivation step comprises, consists essentially of and/or consists of four, five, six, seven, eight, nine, ten or more layers of dry filter paper. Where paper serves as the surface, it may be contained within any suitable vessel, flask, dish (e.g., petri, tissue culture), container, and the like. It is also recognized that the surface to be used in the co-cultivation step may be sterilized before use, using any suitable sterilization method known to those of skill in the art.

Thus, in some embodiments of the present invention, wherein a desiccating or extreme desiccating environment is desired, the co-cultivating can comprise culturing the *Agrobacterium*-inoculated sugar cane tissue on at least one layer of dry filter paper. In other embodiments, the co-cultivating comprises culturing said *Agrobacterium*-inoculated sugar cane tissue on two or more layers of dry filter paper. In still other embodiments of the present invention, co-cultivating comprises culturing said *Agrobacterium*-inoculated sugar cane tissue on a surface in the absence of paper (e.g., in the absence of filter paper).

In addition, in embodiments of the present invention wherein a desiccating or extreme desiccating environment is desired, the co-cultivating can comprise culturing said *Agrobacterium*-inoculated sugar cane tissue on at least one layer of dry paper, wherein the dry paper is changed periodically throughout the co-cultivation. "Periodically," as used herein, means, for example, hourly, daily, every two days, every three days, and the like. Thus, in some embodiments, the co-cultivating comprises culturing said *Agrobacterium*-inoculated sugar cane tissue on at least one layer of dry paper, wherein the dry paper is changed daily during co-cultivation.

In some embodiments, small amounts of sterile water or liquid medium, generally not more than about 20 ul, about 50 ul, about 75 ul, about 100 ul, about 200 ul, about 300 ul, about 400 ul, about 500 ul, about 600 ul, about 700 ul, about 800 ul, about 900 ul or about 1000 ul can be added at the co-cultivation step. The addition of small amounts of sterile water or liquid medium as described herein can be added to slow, reduce or attenuate the rate of desiccation. Thus, in some embodiments, sterile water or liquid medium can be added to the callus tissue at the co-cultivation step in an amount of about 1 µl to about 1000 µl. In other embodiments, sterile water or liquid medium can be added to the callus tissue at the co-cultivation step in an amount of about 1 µl to about 1500 µl. In one embodiment, the amount of liquid added during the co-cultivation step can be combined with any change in the original weight of the inoculated plant material as described below.

In some embodiments, the co-cultivating in a desiccating environment comprises culturing said *Agrobacterium*-inoculated sugar cane tissue on at least one layer of dry paper comprising up to 1000 µl of liquid. In other embodiments, the co-cultivating in a desiccating environment comprises culturing said *Agrobacterium*-inoculated sugar cane tissue on at least one layer of filter paper comprising less than 50 µl of liquid.

During the co-cultivation step, the temperature can be any suitable temperature for co-cultivation as known in the art. Thus, in representative embodiments, the temperature can be in a range from about 15° C. to about 30° C., from about 16° C. to about 29° C., from about 17° C. to about 28° C., from about 18° C. to about 27° C., from about 19° C. to about 26° C.; from about 20° C. to about 28° C., from about 20° C. to about 25° C., from about 21° C. to about 24° C., or from about 22° C. to about 23° C. Thus, in some embodiments, the temperature during co-cultivation can be about 15° C., 16° C., 17° C., 18° C., 19° C., 20° C., 21° C., 22° C., 23° C., 24° C., 25° C., 26° C., 27° C., 28° C., 29° C., 30° C., and the like, and any combination thereof. In some embodiments, the temperature during the co-cultivation step is about 20° C. to about 28° C., and the time period of co-cultivation is about 3 days to about 5 days; in other embodiments, the temperature during the co-cultivation step is about 23° C., about 24° C., or about 25° C. and the time period of co-cultivation is from about 3 days to about 5 days. In other embodiments, the co-cultivation step is about 23° C., about 24° C., or about 25° C. and the time period of co-cultivation is about 3 days. In yet other embodiments, the co-cultivation step is about 23° C., about 24° C., or about 25° C. and the time period of co-cultivation is about 4 days. In still other embodiments, the co-cultivation step is about 23° C., about 24° C., or about 25° C. and the time period of co-cultivation is about 5 days. In some embodiments, the co-cultivation step occurs in the dark (i.e., in the absence of an external light source).

In some embodiments of the invention, following the co-cultivation step and prior to selecting and regenerating transgenic plant parts or plants, the *Agrobacterium*-inoculated callus tissue and/or cell thereof can optionally be allowed to "rest" by culturing the inoculated plant material in a resting medium. As used herein, "resting medium" means a medium for culturing inoculated plant material after co-cultivation that typically comprises agents that are bacteriostatic or bactericidal (e.g., antibiotics, and the like) to *Agrobacterium*. As used herein, "bacteriostatic" means capable of inhibiting the growth or reproduction of bacteria. In contrast, "bactericidal" means capable of killing bacteria outright. The constituents of such a medium are generally known in the art. For example, in some embodiments, the resting medium can be a basal medium (e.g., Murashige and Skoog (MS) medium) supplemented with timentin and/or other antibiotic including, but not limited to, cefotaxime and/or carbenicillin. See also, Zhao et al. (2001) *Molecular Breeding* 8:323-333.

Accordingly, in the resting step, the *Agrobacterium*-inoculated plant tissue (e.g., *Agrobacterium*-inoculated plant tissue) can be cultured in the resting medium for about 1 day to about 15 days, about 2 days to about 14 days, about 2 days to about 12 days, about 2 days to about 11 days, about 2 days to about 10 days, about 3 days to about 10 days, about 4 days to about 10 days, about 5 days to about 10 days, about 6 days to about 9 days, or about 6 days to about 8 days. Thus, following the co-cultivation step, the inoculated plant tissue can be cultured in the resting medium for about 1 day, 2 days, 3 days, 4 days, 5 days, 6 days, 7 days, 8 days, 9 days, 10 days, 11 days, 12 days, 13 days, about 14 days, or about 15 days. In some embodiments, no resting step is included, and instead, following co-cultivation, the plant tissue is subjected to selection as described below. In some embodiments, the selection medium can include at least one compound that suppress the growth of and/or kill the bacteria.

In representative embodiments, following inoculation and co-cultivation, and optionally culturing in a resting medium, subsequent selecting and regenerating steps can be by any methods known in the art. See, e.g., McCormick et al. (1986) *Plant Cell Rep.* 5:81-84. For example, the plant material can be transferred to a medium that includes a selective agent capable of preventing the growth of cells that have not received a target polynucleotide (for example, a polynucleotide encoding a polypeptide of interest and/or a nucleotide sequence conferring resistance to a selection agent) of which at least one expression product is capable of preventing the action of a selective agent to thereby select for transformed plant cells. As used herein, "selecting" means a process in which one or more plants, plant tissues, or plant cells are identified as having one or more properties of interest, for example, a selectable marker or a scorable marker, enhanced insect resistance, increased or decreased carotenoid levels, altered coloration, etc. For example, a selection process can include placing organisms under conditions where the growth of those with a particular genotype will be favored.

The selection step can comprise culturing under selective conditions the plant callus tissue and/or cell thereof that was exposed to the nucleotide sequence of interest, wherein the selective conditions include those that are sufficient for distinguishing a transformed cell from a non-transformed cell. Such conditions will vary with, for example, the type of selectable marker used, the cultivar, and the plant material targeted for transformation, but will generally comprise conditions that favor the growth of transformed cells but inhibit the growth of non-transformed cells.

For example, in representative embodiments, during the selection process, the *Agrobacterium*-inoculated plant material can be exposed to sub-lethal levels of a selective agent for about 2 weeks to about 12 weeks, and then to lethal levels of the selective agent for about 4 weeks to about 30 weeks in a step-wise selection process.

The nucleic acid encoding the selectable marker may be on the same expression cassette as the nucleotide sequence of interest, or may be co-transformed on a separate expression cassette. Selectable markers and selection agents are known in the art. Non-limiting examples of selectable marker nucleic acids used routinely in transformation include the nucleic acid encoding nptII, which confers resistance to kanamycin and related antibiotics (Messing and Vierra (1982) *Gene* 19:259-268; Bevan et al. (1983) *Nature* 304:184-187); the nucleic acid encoding bar, which confers resistance to the herbicide phosphinothricin (White et al. (1990) *Nucleic Acids Res.* 18:1062; Spencer et al. (1990) *Theor. Appl. Genet.* 79:625-631); the nucleic acid encoding hph, which confers resistance to the antibiotic hygromycin (Blochinger and Diggelmann (1984) *Mol. Cell. Biol.* 4:2929-2931); the nucleic acid encoding dhfr, which confers resistance to methatrexate (Bourouis et al. (1983) *EMBO J.* 2(7):1099-1104); the nucleic acid encoding EPSPS, which confers resistance to glyphosate (U.S. Pat. Nos. 4,940,935 and 5,188,642), and the nucleic acid encoding phosphomannose isomerase (PMI), which provides the ability to metabolize mannose (U.S. Pat. Nos. 5,767,378 and 5,994,629).

As described above, embryogenic callus cultures are cultures composed of somatic embryos and/or cells that are differentiated to varying degrees. When induced to further differentiate and regenerate, shoots can arise from these cultures by either embryogenesis or organogenesis or a combination of these two processes.

Thus, plant material growing in the presence of a selective agent can be further manipulated for plant regeneration. As used herein, "regenerate," "regeneration," or "regenerating," (and grammatical variations thereof) means formation of a plant from various plant parts (e.g., plant explants, callus tissue, plant cells) that includes a rooted shoot. The regeneration of plants from various plant parts is well known in the art. See, e.g., *Methods for Plant Molecular Biology* (Weissbach et al., eds. Academic Press, Inc. (1988)); for regeneration of sugar cane plants, see, for example, Arencibia et al. (*Trans. Res.* 7:213-222 (1998)); Elliot et al. (*Plant Cell Rep.* 18:707-714 (1999)); and Enriquez-Obregon et al.

(*Planta* 206:20-27 (1998)). The regenerating step can include selecting transformed plant parts, cells or shoots, rooting the transformed shoots, and growing the plantlets in soil. For example, regenerating plants containing a nucleotide sequence of interest introduced by *Agrobacterium* from leaf explants can be achieved as described by Horsch et al. (1985) *Science* 227:1229-1231. Briefly, transformants are grown in the presence of a selection agent and in a medium that induces the regeneration of shoots (e.g., in sugar cane). See, for example, Fraley et al. (1983) *Proc. Natl. Acad. Sci. USA* 80:4803-4807. This method typically produces shoots within about two weeks to four weeks, and the transformed shoots are then transferred to an appropriate root-inducing medium containing the selective agent and an antibiotic to prevent further bacterial growth. Typically, transformed shoots that root in the presence of the selective agent to form plantlets are then transplanted to soil or other media to allow the production of additional roots. (For references to regeneration of sugar cane, see, Lakshmann et al. *In Vitro Cell Devel Biol* 41:345-363 (2005))

The transgenic plantlets are then propagated in soil or a soil substitute to promote growth into a mature transgenic plant. Propagation of transgenic plants from these plantlets can be performed, e.g., in perlite, peatmoss and sand (1:1:1) or commercial plant potting mix under glasshouse conditions.

Thus, some embodiments of the present invention further comprise regenerating a transformed sugar cane plant from the transformed sugar cane callus tissue or cell thereof In other embodiments, a stably transformed sugar cane plant is produced by regenerating a stably transformed sugar cane plant from the stably transformed sugar cane callus tissue or cell thereof produced using the methods described herein.

The *Agrobacterium*-mediated transformation methods of the present invention are applicable to plants of the genus *Saccharum* (i.e., sugar cane, energy cane) and hybrids thereof, including hybrids between plants of the genus *Saccharum* and those of related genera, such as *Miscanthus, Erianthus, Sorghum* and others. As used herein, "sugar cane" and "*Saccharum* spp." mean any of six to thirty-seven species (depending on taxonomic interpretation) of tall perennial grasses of the genus *Saccharum*. In particular, the plant can be *Saccharum aegyptiacum, Saccharum esculentum, Saccharum arenicol, Saccharum arundinaceum, Saccharum barberi, Saccharum bengalense, Saccharum biflorum, Saccharum chinense, Saccharum ciliare, Saccharum cylindricum, Saccharum edule, Saccharum elephantinum, Saccharum exaltatum, Saccharum fallax, Saccharum fallax, Saccharum floridulum, Saccharum giganteum, Saccharum hybridum, Saccharum japonicum, Saccharum koenigii, Saccharum laguroides, Saccharum munja, Saccharum narenga, Saccharum officinale, Saccharum officinarum, Saccharum paniceum, Saccharum pophyrocoma, Saccharum purpuratum, Saccharum ravennae, Saccharum robustum, Saccharum roseum, Saccharum sanguineum, Saccharum sara, Saccharum sinense, Saccharum spontaneum, Saccharum tinctorium, Saccharum versicolor, Saccharum violaceum, Saccharum violaceum*, and any of the interspecific hybrids and commercial varieties thereof.

Any nucleic acid of interest can be transformed into the *Agrobacterium* strain or other bacterial strain competent for nucleic acid transfer for subsequent transformation of sugar cane using the methods of the present invention. In some embodiments, the nucleic acid will be a polynucleotide construct comprising an expression cassette that comprises functional elements that allow for expression of a polynucleotide of interest in sugar cane following its introduction via the bacterial-mediated transformation methods of the present invention.

An expression cassette can comprise a nucleic acid encoding a polynucleotide that confers a property that can be used to detect, identify or select for transformed plant cells and tissues (e.g., a marker for the selection of transformed cells). The nucleic acid encoding the marker may be on the same expression cassette as the nucleotide sequence of interest, or may be co-transformed on a separate expression cassette. In some embodiments, the nucleic acid encoding the marker can be the nucleotide sequence of interest.

The nucleotide sequence of interest to be introduced into sugar cane tissue and/or cell thereof of using the *Agrobacterium*-mediated transformation methods of the present invention can comprise an expression cassette encoding any polypeptide of interest. Non-limiting examples of polypeptides of interest that are suitable for expression in sugar cane include those resulting in agronomically important traits such as herbicide resistance, virus resistance, bacterial pathogen resistance, insect resistance, nematode resistance, and fungal resistance. See, e.g., U.S. Pat. Nos. 5,569,823; 5,304,730; 5,495,071; 6,329,504; and 6,337,431. Other non-limiting examples of a polypeptide of interest may also be one that results in increases in plant vigor or yield (including polypeptides that allow a plant to grow at different temperatures, soil conditions and levels of sunlight and precipitation), or one that allows identification of a plant exhibiting a trait of interest (e.g., selectable marker nucleic acid, seed coat color, etc.).

In some embodiments, the transformed sugar cane exhibits resistance to an herbicide. A number of nucleic acidss are available, both transgenic and non-transgenic, which confer herbicide resistance. Herbicide resistance is also sometimes referred to as herbicide tolerance. Nucleic acids conferring resistance to an herbicide that inhibits the growing point or meristem, such as an imidazolinone or a sulfonylurea can be suitable. Exemplary nucleic acids in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Nucleic acids coding for resistance to glyphosate are also suitable. See, e.g., U.S. Pat. No. 4,940,835 and U.S. Pat. No. 4,769,061. U.S. Pat. No. 5,554,798 discloses transgenic glyphosate resistant maize plants, which resistance is conferred by an altered 5-enolpyruvyl-3-phosphoshikimate (EPSP) synthase nucleic acid.

Nucleic acids coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable herbicides include those that inhibit photosynthesis, such as a triazine and a benzonitrile (nitrilase). See, U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are nucleic acids that confer resistance to a protox enzyme, or provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Application Publication No. 2001/0016956 and U.S. Pat. No. 6,084,155.

The insecticidal proteins useful for the invention may be expressed in an amount sufficient to control insect pests, i.e., insect controlling amounts. It is recognized that the amount of expression of insecticidal protein in a plant necessary to control insects may vary depending upon the sugar cane cultivar, type of insect, environmental factors and the like. Nucleic acids useful for insect or pest resistance include, for example, nucleic acids encoding toxins identified in *Bacillus* organisms. Nucleic acids encoding *Bacillus thuringiensis* (Bt) toxins from several subspecies have been cloned and recombinant clones have been found to be toxic to lepidopteran, dipteran and coleopteran insect larvae (for example, various delta-endotoxin nucleic acids such as Cry1Aa, Cry1Ab, Cry1Ac, Cry1B, Cry1C, Cry1D, Cry1Ea, CryIFa, Cry3A, Cry9A, Cry9C and Cry9B; as well as nucleic acids encoding vegetative insecticial proteins such as Vip1, Vip2 and Vip3). A full list of Bt toxins can be found on the worldwide web at *Bacillus thuringiensis* Toxin Nomenclature Database maintained by the University of Sussex (see also, Crickmore et al. (1998) *Microbiol. Mol. Biol. Rev.* 62:807-813).

The polypeptide of interest may also be useful for controlling a wide variety of pests including, but not limited to, *Ustilago scitaminea*, sugar cane mosaic virus, *Eldana saccharina, Diatraea saccharalis*, sorghum mosaic virus, etc.

Polypeptides of interest that are suitable for expression in sugar cane further include those that improve or otherwise facilitate the conversion of harvested cane into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the heterologous expression of a cellulase enzyme).

In one embodiment, the polypeptide of interest contributes to improved digestibility for food or feed. Xylanases are hemicellulolytic enzymes that improve the breakdown of plant cell walls, which leads to better utilization of the plant nutrients by the animal. This leads to improved growth rate and feed conversion. Also, the viscosity of the feeds containing xylan can be reduced. Expression of xylanases in plant cells also can also potentially act to facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on Trichoderma reesei Cellulases and Other Hydrolases," Espoo; Souminen and Reinikainen, eds. (1993) *Foundation for Biotechnical and Industrial Fermentation Research* 8:125-135; U.S. Patent Application Publication No. 2005/0208178; and WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In another embodiment, the polypeptide of interest is a polysaccharide degrading enzyme. Such plants may be useful for generating, for example, fermentation feedstocks for bioprocessing. In some embodiments, the enzymes useful for fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include without limitation: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; and starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; g) other enzymes such as α-L-fucosidase (EC 3.2.1.51), α-L-rhamnosidase (EC 3.2.1.40), levanase (EC 3.2.1.65), inulanase (EC 3.2.1.7), and the like.

Further additional enzymes which may be used include proteases, such as fungal and bacterial proteases. Fungal proteases include, for example, those obtained from *Aspergillus, Trichoderma, Mucor* and *Rhizopus*, such as *A. niger, A. awamori, A. oryzae* and *M miehei*. Of particular interest in the present invention are cellobiohydrolase (CBH) enzymes (EC 3.2.1.91). In one embodiment, the cellobiohydrolase enzyme is CBH1 or CBH2.

Other enzymes include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

In other embodiments, the nucleic acid can be a polynucleotide construct comprising an expression cassette that comprises a functional polynucleotide. As used herein, "functional polynucleotide" means a polynucleotide that can be transcribed, but not translated, such as an inhibitory nucleic acid.

Inhibitory nucleic acids can inhibit the expression of a polypeptide of interest such as those described below. The inhibitory nucleic acids may inhibit the expression of a polypeptide directly, by preventing translation of a messenger RNA encoding the polypeptide (for example, sense suppression/cosuppression; antisense suppression; doublestranded RNA (dsRNA) interference via small interfering RNA, micro RNA or short hairpin RNA; amplicon-mediated interference; and ribozymes). In other embodiments, the nucleic acids can encode a polypeptide that inhibits the transcription or translation of a nucleic acid sequence encoding the polypeptide of interest. Methods for inhibiting or eliminating the expression of a gene product in mammalian cells are well known in the art, and any such method may be used in the present invention to inhibit the expression of the polypeptide of interest.

For sense suppression/cosuppression, an expression cassette can be designed to express a cosuppressing nucleic acid molecule corresponding to a native nucleic acid encoding a polypeptide of interest in the "sense" orientation. The cosuppressing nucleic acid molecule can correspond to all or part of the nucleic acid encoding the polypeptide of interest, all or part of the 5' and/or 3' untranslated region of the nucleic acid encoding the polypeptide of interest, or all or part of the coding sequence and untranslated regions of the nucleic acid encoding the polypeptide of interest. In general, the cosuppressing nucleic acid can comprise at least about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950 or 1000 nucleotides, or can be of any size up to and including the full length nucleic acid sequence encoding the polypeptide of interest. Where the cosuppressing nucleic acid comprises all or part of the coding region for the polypeptide of interest, the expression cassette can be designed to eliminate the start codon so that no functional polypeptide of interest will be transcribed from the cosuppressing nucleic acid. Overexpression of the cosuppressing nucleic acid can result in reduced expression of the nucleic acid encoding the polypeptide of interest.

For antisense suppression, an expression cassette can be designed to express an antisense nucleic acid molecule complementary to all or part of a native nucleic acid encoding the polypeptide of interest. The antisense nucleic acid molecule can correspond to all or part of a complement of the nucleic acid encoding the polypeptide of interest, all or part of a complement of the 5' and/or 3' untranslated region of the nucleic acid encoding the polypeptide of interest, or all or part of a complement of both the coding sequence and the untranslated regions of the nucleic acid encoding the polypeptide of interest. The antisense nucleic acid also can be fully complementary (i.e., 100% identical to the complement of the target nucleic acid sequence) or partially complementary (i.e., less than 100% identical to the complement of the target nuclide acid sequence) to the nucleic acid encoding the polypeptide of interest. Expression of the antisense nucleic acid molecule can result in reduced expression of the nucleic acid encoding the polypeptide of interest.

Regardless of the type of antisense nucleic acid used, sequences of at least 15 nucleotides, 20, 25, 30, 35, 40, 45, 50, 75, 100, 150, 200, 250, 300, 350, 400, 450, 500, 550 nucleotides or greater can be used.

Efficiency of antisense suppression can be increased by including a poly-dT region in the expression cassette at a position 3' to the antisense sequence and 5' of the polyadenylation signal. See, U.S. Patent Application Publication No. 2002/0048814.

For dsRNA interference, a sense nucleic acid molecule like that described above for cosuppression and an antisense nucleic acid molecule fully or partially complementary to the sense nucleic acid sequence are expressed in the same cell, resulting in inhibition of the expression of a native nucleic acid encoding the polypeptide of interest. Expression of the sense and antisense nucleic acid molecules can be accomplished by designing an expression cassette to comprise both sense and antisense sequences for the nucleic acid encoding the polypeptide of interest. Alternatively, separate expression cassettes can be used for the sense and antisense nucleic acid molecule.

Regardless of the type of nucleic acid used for dsRNA interference, sequences of at least 15 nucleotides, 20, 25, 30, 35, 40, 45, 50, 75, 100, 150, 200, 250, 300, 350, 400, 450, 500, 550 nucleotides or greater can be used.

For amplicon-mediated interference, an amplicon expression construct can be designed having a nucleic acid sequence comprising a virus-derived sequence that contains all or part of a native nucleic acid encoding the polypeptide of interest. The viral sequences present in the transcription product of the amplicon expression cassette allow the transcription product to direct its own replication. The transcripts produced by the amplicon may be either sense or antisense relative to the nucleic acid sequence encoding the polypeptide of interest.

Regardless of the type of nucleic acid used for amplicon-mediated interference, sequences of at least 15 nucleotides, 20, 25, 30, 35, 40, 45, 50, 75, 100, 150, 200, 250, 300, 350, 400, 450, 500, 550 nucleotides or greater can be used.

For ribozymes, an expression construct can be designed to express a nucleic acid molecule having catalytic activity toward a mRNA expressed by a native nucleic acid sequence encoding the polypeptide of interest. The catalytic nucleic acid causes the degradation of the mRNA or nucleic acid encoding the polypeptide of interest resulting in reduced expression of the polypeptide of interest.

Regardless of the type of nucleic acid used for ribozymes, sequences of at least 15 nucleotides, 20, 25, 30, 35, 40, 45, 50, 75, 100, 150, 200, 250, 300, 350, 400, 450, 500, 550 nucleotides or greater can be used.

For micro RNA (miRNA) interference, an expression construct can be designed to express a nucleic acid molecule complimentary to a native nucleic acid sequence encoding the polypeptide of interest, such that the miRNA is transcribed, but not translated into the poypeptide of interest (i.e., a non-coding RNA). Each primary transcript (a pri-miRNA) is processed into a short stem-loop structure called a pre-miRNA and finally into a functional miRNA. miRNAs consist of about twenty-two to about twenty-three ribonucleotides. Mature miRNA are highly efficient at inhibiting the expression of the nucleic acid encoding the polypeptide of interest. Because mature miRNA molecules are partially complementary to one or more nucleic acid molecules encoding the polypeptide of interest, they down-regulate gene expression by inhibiting translation or sometimes facilitating cleavage of nucleic acid molecules encoding polypeptide of interest.

For short hairpin RNA (shRNA) interference, an expression cassette can be designed to express a nucleic acid molecule complimentary to a native nucleic acid encoding the polypeptide of interest that makes a tight hairpin turn that can be used to silence gene expression via RNA interference. shRNA interference also can be intron-containing hairpin RNA (ihpRNA) interference in which the expression cassette can be designed to express a nucleic acid encoding intron-spliced RNA with a hairpin structure.

Regardless of the type of shRNA used, sequences of at least 15 nucleotides, 20, 25, 30, 35, 40, 45, 50, 75, 100, 150, 200, 250, 300, 350, 400, 450, 500, 550 nucleotides or greater can be used.

The expression cassette for shRNA interference also can be designed such that the sense sequence and antisense sequence do not correspond to a nucleic acid sequence encoding the polypeptide of interest. Instead, the sense and antisense sequences flank a loop sequence that comprises a nucleotide sequence corresponding to all or part of the nucleic acid sequence encoding the polypeptide of interest. Thus, the loop region determines the specificity of the RNA interference. See, e.g., Int'l Patent Application Publication No. WO 02/00904.

In addition, transcriptional gene silencing (TGS) can be accomplished through use of shRNA molecules where an inverted repeat of the hairpin shares sequence identity with the promoter region of a nucleic acid encoding the polypeptide of interest to be silenced. Processing of the shRNA into short RNAs that can interact with the homologous promoter region may trigger degradation or methylation to result in silencing (see, for example, Aufsatz et al. *Proc. Natl. Acad. Sci.* 99:16499-16506 (2002), and Mette et al. *Embo J.* 19:5194-5201 (2000)).

It will also be recognized that a nucleotide sequence of interest may be optimized for increased expression in the transformed sugar cane cell. That is, the nucleotide sequences can be synthesized using sugar cane-preferred codons for improved expression, or may be synthesized using codons at a sugar cane-preferred codon usage frequency. Generally, the GC content of the nucleic acid will be increased as compared with a typical non-plant/non-sugar cane nucleotide sequence. See, e.g., Campbell & Gowri (1990) *Plant Physiol.* 92:1-11 for a discussion of host-preferred codon usage. Methods are available in the art for synthesizing plant-preferred nucleic acids. See, e.g., U.S. Pat. Nos. 5,380,831, and 5,436,391, and Murray et al. (1989) *Nucleic Acids Res.* 17:477-498, herein incorporated by reference.

Accordingly, in some embodiments of the invention transformation of callus tissue and/or a cell thereof comprises transformation with one or more nucleotide sequences of interest. In some embodiments, the nucleotide sequence(s) of interest encodes a polypeptide of interest and/or a functional polynucleotide of interest. In other embodiments, the nucleotide sequence of interest is comprised within an expression cassette.

The methods of the invention therefore comprise transformation of plant tissue with one or more nucleic acid molecules of interest. In one embodiment, the nucleic acid comprises an expression cassette that comprises a nucleotide sequence encoding a polypeptide of interest and/or a functional polynucleotide of interest. As used herein, "expression cassette" means a nucleic acid molecule capable of directing expression of a particular nucleotide sequence in a sugar cane cell, comprising a promoter operably linked to the nucleotide sequence of interest, which is optionally operably linked to termination signals. It also typically comprises sequences required for proper translation of the nucleotide sequence of interest. The coding region usually codes for a polypeptide of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the sugar cane plant, e.g., the particular DNA sequence of the expression cassette does not occur naturally in a sugar cane plant and is introduced into the sugar cane plant, or an ancestor of the sugar cane plant, by a transformation event. Alternatively, the expression cassette is endogenous to the sugar cane plant. In some embodiments, the expression of the nucleotide sequence of interest in the expression cassette may be under the control of a constitutive promoter or of an inducible promoter that initiates transcription only when the sugar cane plant or plant part thereof is exposed to some particular external stimulus. In other embodiments, the promoter can also be exclusively or preferentially expressed in specific cells, specific tissues, or specific organs or exclusively or preferentially expressed in a particular stage of development.

The expression cassette may include in the 5'-3' direction of transcription, a transcriptional and translational initiation region (i.e., a promoter) and a polynucleotide of interest. The expression cassette may optionally comprise a transcriptional and translational termination region (i.e., termination region) functional in plants. In some embodiments, the expression cassette further comprises a nucleotide sequence encoding a nucleic acid which confers resistance to a selection agent (e.g., selectable marker nucleic acid), which allows for the selection for stable transformants. In still further embodiments, expression constructs of the invention can also comprise a leader sequence and/or a sequence allowing for inducible expression of the polynucleotide of interest. See, Guo et al. ((2003) *Plant J.* 34:383-92) and Chen et al. ((2003) *Plant J.* 36:731-40) for examples of sequences allowing for inducible expression.

The regulatory sequences of the expression construct are operably linked to the polynucleotide of interest. As used herein, "operably linked", when referring to a first nucleic acid sequence that is operably linked with a second nucleic acid sequence, means a situation when the first nucleic acid sequence is placed in a functional relationship with the second nucleic acid sequence. For instance, a promoter is operably linked to a coding sequence if the promoter effects the transcription or expression of the coding sequence. Generally, operably linked nucleic acid sequences are contiguous and, where necessary to join two protein coding regions, the open reading frames are aligned.

Any promoter capable of driving expression in the plant of interest may be used in the practice of the invention. The promoter may be native or analogous, or foreign or heterologous, to the sugar cane plant into which the expression cassette will be introduced. The terms "heterologous" and "exogenous" when used herein to refer to a nucleic acid sequence (e.g., a DNA or RNA sequence), refer to a sequence that originates from a source foreign to the particular plant (e.g., foreign to the sugar cane plant) or, if from the same source, is modified from its original form. Thus, for example, a heterologous nucleic acid in a sugar cane cell includes a nucleic acid that is endogenous to the particular cell but has been modified through, for example, the use of DNA shuffling. The terms heterologous or exogenous nucleic acid also includes non-naturally occurring multiple copies of a naturally occurring DNA sequence. Thus, these terms refer to a DNA segment that is foreign or heterologous to the cell, or homologous to the sugar cane cell but in a position within the cell's genome in which the element is not ordinarily found. Exogenous/heterologous DNA segments are expressed to yield exogenous/heterologous polypeptides or functional polynucleotides.

A "homologous" nucleic acid sequence is a nucleic acid (e.g., DNA or RNA) sequence naturally associated with a sugar cane cell into which it is introduced.

The choice of promoters to be included in an expression cassette depends upon several factors, including, but not limited to, efficiency, selectability, inducibility, desired expression level, and cell- or tissue-preferential expression. It is a routine matter for one of skill in the art to modulate the expression of an operably linked sequence by appropriately selecting and positioning promoters and other regulatory regions relative to that sequence.

Some suitable promoters initiate transcription only, or predominantly, in certain cell types. Thus, as used herein a cell type- or tissue-preferential promoter is one that drives expression preferentially in the target sugar cane tissue, but may also lead to some expression in other cell types or tissues as well. Methods for identifying and characterizing promoter regions in plant genomic DNA include, for example, those described in the following references: Jordano et al. (1989) *Plant Cell* 1:855-866; Bustos et al. (1989) *Plant Cell* 1:839-854; Green et al. (1988) *EMBO J.* 7:4035-4044; Meier et al. (1991) *Plant Cell* 3:309-316; and Zhang et al. (1996) *Plant Physiology* 110:1069-1079.

Promoters active in photosynthetic tissue in order to drive transcription in green tissues such as leaves and stems are also contemplated for the present invention, for example, promoters that drive expression only or predominantly in such tissues. The promoter may confer expression constitutively throughout the plant, or differentially with respect to the green tissues, or differentially with respect to the developmental stage of the green tissue in which expression occurs, or in response to external stimuli.

Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.* 35:773-778), the Cab-1 promoter from wheat (Fejes et al. (1990) *Plant Mol. Biol.* 15:921-932), the CAB-1 promoter from spinach (Lubberstedt et al. (1994) *Plant Physiol.* 104:997-1006), the cab1R promoter from rice (Luan et al. (1992) *Plant Cell* 4:971-981), the pyruvate orthophosphate dikinase (PPDK) promoter from corn (Matsuoka et al. (1993) *Proc. Natl. Acad. Sci. USA* 90:9586-9590), the tobacco Lhcb1*2 promoter (Cerdan et al. (1997) *Plant Mol. Biol.* 33:245-255), the Arabidopsis thaliana SUC2 sucrose-H+symporter promoter (Truernit et al. (1995) *Planta* 196: 564-570), and thylakoid membrane protein promoters from spinach (psaD, psaF, psaE, PC, FNR, atpC, atpD, cab, rbcS). Other promoters that drive transcription in stems, leaves and green tissue are described in U.S. Patent Publication No. 2007/0006346, herein incorporated by reference in its entirety.

A maize nucleic acid encoding phosphoenol carboxylase (PEPC) has been described in Hudspeth and Grula (1989) *Plant Molec. Biol* 12:579-589. Using standard molecular biological techniques the promoter for this nucleic acid can be used to drive the expression of any nucleic acid in a green tissue-specific manner in transgenic plants.

In some other embodiments of the present invention, inducible promoters may be desired. Inducible promoters drive transcription in response to external stimuli such as chemical agents or environmental stimuli. For example, inducible promoters can confer transcription in response to hormones such as gibberellic acid or ethylene, or in response to light or drought.

As described above, an expression cassette can optionally include transcriptional terminators. A variety of transcriptional terminators are available for use in expression cassettes. These are responsible for the termination of transcription beyond the coding region of a polynucleotide of interest within the expression cassette and correct mRNA polyadenylation. The termination region may be native with the transcriptional initiation region, may be native with the operably linked DNA sequence of interest, may be native with the sugar cane plant, or may be derived from another source (i.e., foreign or heterologous to the promoter, the DNA sequence of interest, the sugar cane plant, or any combination thereof). Appropriate transcriptional terminators are those that are known to function in plants and include the CAMV 35S terminator, the tml terminator, the nopaline synthase terminator, and the pea rbcs E9 terminator. In addition, a nucleic acid's native transcription terminator may be used.

As described above, in some embodiments, an expression cassette can further comprise a nucleic acid encoding a nucleotide sequence, which confers resistance to a selection agent (i.e., selectable marker nucleic acid); thus, allowing for the selection of transformed callus tissue/cells. The selectable marker nucleic acid may be on the same expression cassette as the nucleotide sequence of interest, or may be co-transformed on a separate expression cassette. Any selectable marker nucleic acid known to those of skill in the art can be used in the methods of the present invention.

Thus, in some embodiments of the present invention, when the sugar cane callus tissue or cell thereof is inoculated with *Agrobacterium* (or other bacteria capable to transferring nucleic acids to plants) comprising a nucleic acid which confers resistance to a selection agent, the inoculated sugar cane callus tissue or cell thereof can be cultivated in the presence of the selection agent to select the transformed sugar cane callus tissue or cell thereof (i.e., those tissues and cells having incorporated the nucleic acid which confers resistance to the selection agent). In some embodiments, the nucleic acid which confers resistance to a selection agent is selected from the group consisting of pmi, neo, bar, pat, ALS, HPH, HYG, EPSPS, Hml, and any combination thereof.

Numerous nucleotide sequences have been found to enhance nucleic acid expression from within the transcriptional unit and these nucleotide sequences can be used in conjunction with the expression cassettes of this invention to increase the expression of a polynucleotide of interest in transgenic sugar cane plants and plant parts thereof (e.g., callus tissue and/or cell thereof).

Various intron sequences have been shown to enhance expression, particularly in monocotyledonous cells. Intron 1 of the maize alcohol dehydrogenase gene was found to be particularly effective and enhanced expression in fusion constructs with the chloramphenicol acetyltransferase gene (Callis et al. (1987) *Genes Develop.* 1:1183-1200). Intron sequences have been routinely incorporated into plant transformation vectors, typically within the non-translated leader.

A number of non-translated leader sequences derived from viruses are also known to enhance expression, and these are encompassed herein. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (see, for example, Gallie et al. (1987) *Nucleic Acids Res.* 15:8693-8711; Skuzeski et al. (1990) *Plant Molec. Biol.* 15:65-79). Other leader sequences known in the art include, but are not limited to, picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Allison et al. (1986) *Virology* 154:9-20; and Gallie et al. (1995) *Gene* 165:233-238);

MDMV leader (Maize Dwarf Mosaic Virus; Allison et al. (1986) *Virology* 154:9-20); human immunoglobulin heavy-chain binding protein (BiP) leader (Macejak and Samow (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV; Gallie et al. (1987) *Nucleic Acids Res.* 15:3257-3273; Gallie et al. (1988) *Nucleic Acids Res.* 16:883-893; Gallie et al. (1992) *Nucleic Acids Res.* 20:4631-4638); and Maize Chlorotic Mottle Virus leader (MCMV; Lommel et al. (1991) *Virology* 81:382-385). See also, Della-Cioppa et al. (1987) *Plant Physiology* 84:965-968.

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins, which is cleaved during chloroplast import to yield the mature protein (see, e.g., Comai et al. (1988) *J. Biol. Chem.* 263:15104-15109). These signal sequences can be fused to heterologous gene products to effect the import of heterologous products into the chloroplast (van den Broeck et al. (1985) *Nature* 313:358-363). DNA encoding for appropriate signal sequences can be isolated from the 5' end of the cDNAs encoding the RUBISCO protein, the CAB protein, the EPSP synthase enzyme, the GS2 protein and many other proteins that are known to be chloroplast localized. See also, the section entitled "Expression with Chloroplast Targeting" in Example 37 of U.S. Pat. No. 5,639,949.

The above-described targeting sequences can be utilized not only in conjunction with their endogenous promoters, but also in conjunction with heterologous promoters. Use of promoters heterologous to the targeting sequence allows the targeting of a nucleic acid along with a promoter having an expression pattern different to that of the promoter from which the targeting signal is derived.

In order to ensure localization to the plastids, a transit peptide can be used. A non-limiting example of a transit peptide is the transit peptide from plastidic Ferredoxin: NADP+oxidoreductase (FNR) of spinach, which is disclosed in Jansen et al. (1988) *Current Genetics* 13:517-522. In particular, the sequence ranging from the nucleotides −171 to 165 of the cDNA sequence disclosed therein can be used, which comprises the 5' non-translated region as well as the sequence encoding the transit peptide. Another non-limiting example of a transit peptide is that of the waxy protein of maize including the first 34 amino acid residues of the mature waxy protein (Klosgen et al. (1989) *Mol. Gen. Genet.* 217:155-161). It is also possible to use this transit peptide without the first 34 amino acids of the mature protein. Furthermore, the signal peptides of ribulose bisphosphate carboxylase small subunit (Wolter et al. (1988) *Proc. Natl. Acad. Sci. USA* 85:846-850; Nawrath et al. (1994) *Proc. Natl. Acad. Sci. USA* 91:12760-12764), NADP malate dehydrogenase (Galiardo et al. (1995) *Planta* 197:324-332), glutathione reductase (Creissen et al. (1995) *Plant J.* 8:167-175) and/or R1 protein (Lorberth et al. (1998) *Nature Biotechnology* 16:473-477) can be used.

As described above, some embodiments of the present invention lead to regeneration of green plantlets and plants with photosynthetic ability. The test used for confirmation that the nucleotide sequence of interest is stably integrated into the genome of the sugar cane plant depends on the property to be conferred to the plant. For example, when the property is herbicide resistance, confirmation may be achieved by treatment of the growing plants by spraying or painting the leaves with the herbicide in a concentration that is lethal for control plants that have not been subjected to the transformation process.

Where the transferred nucleotide sequence of interest encodes a polypeptide of interest, expression of that polypeptide in the transformed sugar cane plant can be detected using an immunological method. Immunological methods that can be used include, but are not limited to, competitive and non-competitive assay systems using immune-based techniques such as Western blots, radioimmunoassays, ELISA (enzyme linked immunosorbent assay), multiplex ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and known in the art (see, e.g., *Current Protocols in Molecular Biology*, Vol. 1 (Ausubel et al., eds. John Wiley & Sons, Inc., New York (1994)), which is incorporated by reference herein in its entirety).

In additional embodiments, expression can be measured by evaluating patterns of expression of the polynucleotide encoding the polypeptide of interest, or of reporter nucleic acids, or both. For example, expression patterns can be evaluated by Northern analysis, polymerase chain reaction (PCR), reverse-transcription PCR (RT-PCR), Taq Man expression assay (Applied Biosystems, Inc; Foster City, Calif.), ribonuclease protection assays, fluorescence resonance energy transfer (FRET) detection, monitoring one or more molecular beacons, hybridization to an oligonucleotide array, hybridization to a cDNA array, hybridization to a polynucleotide array, hybridization to a liquid microarray, hybridization to a microelectric array, cDNA sequencing, clone hybridization, cDNA fragment fingerprinting, and the like. The particular method elected will be dependent on such factors as quantity of RNA recovered, artisan preference, available reagents and equipment, detectors, and the like. Such assays are routine and known in the art (see, e.g., Ausubel et al., supra).

Where the transferred nucleotide sequence is a functional polynucleotide, the presence and/or efficacy of the polynucleotide in a transformed sugar cane plant can be detected using any suitable method known in the art, including the molecular assays described above. For example, molecular assays that can be used include, but are not limited to, Northern analysis, polymerase chain reaction (PCR), reverse-transcription PCR (RT-PCR), Taq Man expression assay (Applied Biosystems, Inc; Foster City, Calif.), ribonuclease protection assays, fluorescence resonance energy transfer (FRET) detection, monitoring one or more molecular beacons, hybridization to an oligonucleotide array, hybridization to a cDNA array, hybridization to a polynucleotide array, hybridization to a liquid microarray, hybridization to a microelectric array, cDNA sequencing, clone hybridization, cDNA fragment fingerprinting, and the like.

The *Agrobacterium*-mediated transformation methods of the present invention can advantageously increase *Agrobacterium*-mediated transformation efficiency in sugar cane when compared to that obtained using the same inoculation and selection protocols, but using a standard co-cultivation protocol, (e.g., wherein the tissue or cell thereof is more than 28 days post-initiation).

Thus, in some embodiments, a method of transforming a sugar cane tissue or cell thereof is provided, the method comprising: (a) inoculating a sugar cane callus tissue or a cell thereof that is less than 28 days post-initiation with an

*Agrobacterium* comprising a nucleotide sequence of interest; and (b) co-cultivating the *Agrobacterium* and the sugar cane callus tissue or a cell thereof to produce a transformed sugar cane callus tissue or cell thereof, wherein transformation efficiency is increased as compared with a control in which the callus tissue is 28 days or more post-initiation. Thus, in some embodiments, a control would comprise inoculating a sugar cane callus tissue or a cell thereof that is 28 days or more post-initiation with an *Agrobacterium* comprising a nucleotide sequence of interest; (b) co-cultivating the *Agrobacterium* and the sugar cane callus tissue or a cell thereof to produce a transformed sugar cane callus tissue or cell thereof; and (c) regenerating a stably transformed sugar cane plant.

In some embodiments, transformation efficiency is increased by at least about 5%, 10%, 15%, 20%, or 25%. In other embodiments, transformation efficiency is increased by at least about 30%, 35%, 40%, 45%, 50%, or more. Transformation efficiency is calculated as the number of events (e.g., the number of transgenic plants) obtained per gram of starting sugar cane plant tissue.

In additional embodiments, a method of transforming a sugar cane callus tissue or cell thereof is provided, the method comprising: (a) inoculating a sugar cane callus tissue or a cell thereof that is less than 28 days post-initiation with an *Agrobacterium* comprising a nucleotide sequence of interest; (b) co-cultivating the *Agrobacterium* and the sugar cane callus tissue or a cell thereof to produce a transformed sugar cane callus tissue or cell thereof; and (c) regenerating a stably transformed sugar cane plant, wherein regeneration rate of stably transformed sugar cane plants is increased as compared with a control in which the callus tissue is 28 days or more post-initiation, as described above.

In further embodiments, a method of transforming a sugar cane callus tissue or a cell thereof is provided, the method comprising: (a) inoculating a sugar cane callus tissue or a cell thereof that is less than 28 days post-initiation with an *Agrobacterium* comprising a nucleotide sequence of interest; and (b) co-cultivating the *Agrobacterium* and the sugar cane callus tissue to produce a transformed sugar cane callus tissue or cell thereof, wherein nucleic acid delivery to the sugar cane is increased as compare to a control in which the callus tissue is 28 days or more post-initiation, as described above.

The present invention will now be described with reference to the following examples. It should be appreciated that these examples are for the purpose of illustrating aspects of the present invention, and do not limit the scope of the invention as defined by the claims.

EXAMPLES

Example 1

Comparison of Transformation Sugar Cane Tissue Derived from Variety Q117 Obtained from Different Initiation Batches and Transformed Using *Agrobacterium* at Different Tissue Ages (Days Post-Initiation)

Plant Source and Material:

Leaf whorl material from field grown sugar cane plants was collected and initiated on EM3 medium (see below). Transverse sections (approximately 20) of immature leaf whorl between 1-3 mm in thickness were taken from just above the meristem and placed in the top-up orientation, Cultures were either used immediately or maintained in the dark at 25-27° C. for 0 to about 45 days. Plant material made up of leaf explants and/or cells of the explants were utilized for transformation either immediately or within 4-10 days of the last subculture.

Preparation of *Agrobacterium*:

*Agrobacterium* cultures harboring a vector comprising nptII (selectable marker) were streaked out on LB medium (see below) containing appropriate antibiotics and grown at 28° C. for 3 days and then stored at 4° C. for up to 1 month. Prior to transformation, a single colony was selected and streaked onto a fresh LB plate and grown for 1-2 days at 28° C.

An *Agrobacterium* culture was initiated in 30 ml of AB medium (see below) or LB medium from an isolated colony and grown for 4-5 hours at 28° C. in a shaker at 200 revolutions per minute (RPM). The culture was transferred to a 500 ml Erlenmeyer flask with 100-150 ml of fresh AB or LB medium. The culture grown for 12-14 hours in 28° C. with 150 RPM to an optical density (OD) of 0.2-1.0 at 600 nm.

The *Agrobacterium* culture was then centrifuged for 20 minutes at 2000 RPM at 25° C. The pellet obtained was resuspended in 150 ml ½ strength Murashige & Skoog (MS) medium (without sucrose) supplemented with 400 µM of acetosyringone. This culture was then maintained at 28° C. at 150 RPM for 4 hours prior to infection. OD was adjusted to a desired level before infection of the plant material to be transformed.

Infection and Co-Cultivation:

Callus tissue was weighed to ensure all experiments could be compared. Approximately 10 g of callus tissue was used per treatment and was placed into a 200 ml culture vessel. Callus tissue was heat shocked (not done for Q208) at 45° C. for 5 minutes by adding 50 ml of pre-warmed ½ strength MS (without sucrose) medium and then maintaining the callus in a water bath at 45° C. MS medium was then drained from the callus tissue, and 25 ml of the *Agrobacterium* inoculation suspension was added to each vessel and mixed gently. The callus/*Agrobacterium* mixture was vacuum-infiltrated by placing it into a vacuum chamber for 10 minutes at −27.5 mmHg of vacuum. The callus/*Agrobacterium* mixture was then rested for 5-10 minutes in the dark.

The *Agrobacterium* inoculation suspension was then drained from the callus, and the remaining callus culture was blotted dry to remove excess *Agrobacterium* inoculation suspension. Plant tissues were blotted on filter paper such as Whatman Grade 1 paper, until the *Agrobacterium* inoculation suspension was substantially removed. The callus was then transferred for co-cultivation to 90×25-mm petri dishes and sealed with NESCOFILM®, MICROPORE™ tape (3M; Minneapolis, Minn.) or similar material. The dishes were incubated in the dark at 22° C. for 2-3 days.

Post-Transformation:

After co-cultivation, the callus tissue was transferred to MS 1 medium (see below) containing with 200 mg/L of timentin ("resting" medium) and kept in the dark at 25° C. for 4 days. The first selection step was made in MS 2 medium (see below) containing 50 mg/L of geneticin and 200 mg/L of timentin for 14-15 days in the dark at 25° C.

Regeneration and Rooting:

Regeneration was conducted on MS 3 medium (see below) supplemented with 50 mg/L of geneticin and 200 mg/L of timentin at 25° C. in 16 hr light. Gradual increases in light intensity were required. For the first week, the culture was left on a laboratory bench under normal room lighting, and for the next 3 weeks, the culture was grown at moderate light intensity.

Shoot formation was seen between 2-4 weeks. When the first leaves appeared, the shoots were transferred to MS 4 medium (see below) until the plants grew to 4-5 cm in height. They were then sampled for analysis and transferred to soil.

Media: The components within the media referred to above are as follows.

EM3: MS salts and vitamins; 0.5 g/L casein hydrolysate; 100 ml/L coconut water; 20 g/L sucrose and 3 mg/12,4-D.

LB basic: 10 g/L NaCl; 5 g/L yeast extract; and 10 g/L tryptone.

LB solid: LB basic with 15 g/L of agar.

AB: The following salts were autoclaved and added: 2 g/L $(NH_4)_2SO_4$; 6 g/L $Na_2HPO_4$; 3 g/L $KH_2PO_4$; and 3 g/L NaCl. The following compounds were filter sterilized: 0.1 mM $CaCl_2$; 1.0 mM $MgCl_2$; 0.003 mM $FeCl_3$; and 5 g/L glucose.

MS basic: MS medium salts and vitamins, with 25 g/L sucrose.

MS 1: MS basic supplemented with 3.0 mg/L 2,4-D and 200 mg/L Timentin.

MS 2: MS basic supplemented with 3.0 mg/L 2,4-D and 50 mg/L Geneticin and 200 mg/L Timentin.

MS 3: MS basic supplemented with 40 ml of coconut water filter sterilized and 1.0-2.0 mg/L BAP (cultivar dependent, thus not required for all cultivars) and 50 mg/L Geneticin and 200 mg/L Timentin.

MS 4: MS basic supplemented with 1.0 g/L charcoal and 1.0 mg IBA (indole-3-butyric acid, not required for all cultivars and 50 mg/L Geneticin.

CoCult: Media co-cultivation media as described for banana in Khanna et al. *Molecular Breeding* 14(3): 239-252 (2004).

The transformation vector pUbiNptII(s) contains an expression cassette between the left and right borders of the transformation vector. This expression cassette contains the following elements operably linked together: maize ubiquitin promoter linked to a nucleic acid sequence encoding the protein NptII which confers geneticin resistance, followed by the Nos terminator sequence.

Table 1 shows the results of an experiment comparing the results of transforming sugar cane tissue derived from variety Q117 obtained from different initiation batches and transformed using *Agrobacterium* at different tissue ages (days post-initiation). The number of transformants was determined by the number of plants producing roots on media containing the selective agent. Previous work has shown that greater than 95% of plants that form roots on selection are transgenic as determined by molecular testing.

TABLE 1

The effect of callus age on the number of transformed plants produced.

| Variety | Construct | Sugar cane tissue age (days post-initiation) | # of Transformed Plants |
|---------|-----------|----------------------------------------------|-------------------------|
| Q117 | pUbiNptII(s) | 15 days | 28 |
| Q117 | pUbiNptII(s) | 29 days | 55 |
| Q117 | pUbiNptII(s) | 43 days | 23 |
| Q117 | pUbiNptII(s) | 16 days | 48 |
| Q117 | pUbiNptII(s) | 30 days | 25 |
| Q117 | pUbiNptII(s) | 43 days | 11 |
| Q117 | pUbiNptII(s) | 58 days | 7 |
| Q117 | pUbiNptII(s) | 6 days | 11 |
| Q117 | pUbiNptII(s) | 26 days | 45 |
| Q117 | pUbiNptII(s) | 40 days | 33 |

TABLE 1-continued

The effect of callus age on the number of transformed plants produced.

| Variety | Construct | Sugar cane tissue age (days post-initiation) | # of Transformed Plants |
|---------|-----------|----------------------------------------------|-------------------------|
| Q117 | pUbiNptII(s) | 13 days | 24 |
| Q117 | pUbiNptII(s) | 33 days | 13 |
| Q117 | pUbiNptII(s) | 47 days | 9 |

Example 2

Comparison of the Frequency of Transformation of a Single Line of Sugar Cane Q117 Tissue Transformed Every Week from 6 Days Post-Initiation to 60 Days Post-Initiation In a further experiment a single line of sugar cane Q117 tissue was transformed every week from 6 days post-initiation to 60 days post-initiation and the frequency of transformation was compared between the sugar cane tissue of various ages (i.e., days post-initiation) (see, Table 2). The same callus batch resulting from a single initiation of cane into tissue culture is used in each experiment. This corrects for the slightly different behavior of callus that occurs between initiation batches.

TABLE 2

The effect of callus age on the number of transformed plants produced in a single line of sugar cane tissue.

| Variety | Condition | Amount | Construct | # of Transformed Plants |
|---------|-----------|--------|-----------|-------------------------|
| Q117 | Control 22 days | 1 plate (Approx 1 g) | Untransformed Control | Normal Regeneration >20 plants |
| Q117 | 6 Days | 20 g | pUbiNptII(s) | 11 |
| Q117 | 13 Days | 20 g | pUbiNptII(s) | 25 |
| Q117 | 22 Days | 20 g | pUbiNptII(s) | 24 |
| Q117 | 29 Days | 20 g | pUbiNptII(s) | 42 |
| Q117 | 36 Days | 20 g | pUbiNptII(s) | 31 |
| Q117 | 43 Days | 20 g | pUbiNptII(s) | 29 |
| Q117 | 50 Days | 20 g | pUbiNptII(s) | Contaminated |
| Q117 | 60 Days | 18 g | pUbiNptII(s) | 20 |

Q117 shows the same trend as observed for other, more difficult to transform varieties, but Q117 retains useful transformation across a much larger range of callus ages (see Examples 3 and 4, below). The high level of transformation efficiency across a broad callus age range highlights why Q117 is used as a model for transformation. However, it is noted that a peak number of events is observed at a younger age than the commonly used age of 8-10 weeks (Joyce et al. *Plant Cell Rep.* 29:173-183 (2010); Elliott et al. *Austral. J. Plant Physiol.* 25:739-743 (1998)). Thus, the sugar cane variety, Q117, can be transformed efficiently using the methods of the present invention.

Example 3

Comparison of the Transformation Efficiency for Two Different Sugar Cane Varieties at 7 Days and 14 Days Post-Initiation Two different sugar cane genotypes, Q208 and Q232, were compared with regard to transformation efficiency at both 7 days and 14 days post-initiation. The data are shown in Table 3.

TABLE 3

Transformation efficiency for two different sugar cane varieties at 7 days and 14 days post-initiation.

| Condition | Variety (initiation) | Amount | Construct | # of Events |
|---|---|---|---|---|
| Control | Q208 | 1 plate (Approx 1 g) | Untransformed Control | Normal Regeneration >50 plants |
| Q208-14 day | Q208 | 10 g | pUbiNptII(s) | 3 |
| Q208-7 day | Q208 | 10 g | pUbiNptII(s) | 11 |
| Q232-14 day | Q232 | 10 g | pUbiNptII(s) | 0 |
| Q232-7 day | Q232 | 10 g | pUbiNptII(s) | 1 |

Q208 showed good transformation efficiency using the methods of the present invention. Transformation efficiency of Q232 was lower than for Q208 but still useful with at least one event.

Example 4

Comparison of Four Different Sugar Cane Varieties Initiated Each Week for Six Weeks from Zero Days Post-Initiation to 35 Days Post-Initiation and Transformed on the Same Day Four different cane varieties, Q117, Q208, KQ228 and Q232, were initiated once each week for 6 weeks (ages day 0 to day 35). The transformation of the callus took place on the same day. Thus, when used for transformation the callus was 0 days to 35 days post-initiation. This provides a more robust treatment of the age and variety differences and allows the use of the same *Agrobacterium* prep for the entire experiment. The use of callus from additional individual initiations may contribute to additional variability in this aspect of the experiment. The data is shown in Table 4.

TABLE 4

Comparison of transformation for four different sugar cane varieties using callus of various ages from zero to thirty five days post initiation.

| Variety | Condition | Amount | Construct | # of Events |
|---|---|---|---|---|
| Q117 | Control | 1 plate (Approx 1 g) | Untransformed Control | Normal Regeneration >20 plants |
| Q117 | 35 Days | 20 g | pUbiNptII(s) | 40 |
| Q117 | 28 Days | 20 g | pUbiNptII(s) | 27 |
| Q117 | 22 Days | 20 g | pUbiNptII(s) | 31 |
| Q117 | 13 Days | 9 g | pUbiNptII(s) | 14 |
| Q117 | 6 Days | 20 g | pUbiNptII(s) | 24 |
| Q117 | 0 Days | 20 g | pUbiNptII(s) | 5 |
| Q208 | Control | 1 plate (Approx 1 g) | Untransformed Control | Normal Regeneration >20 Plants |
| Q208 | 35 Days | 20 g | pUbiNptII(s) | 0 |
| Q208 | 28 Days | 20 g | pUbiNptII(s) | 1 |
| Q208 | 22 Days | 20 g | pUbiNptII(s) | 2 |
| Q208 | 13 Days | 20 g | pUbiNptII(s) | 4 |
| Q208 | 6 Days | 20 g | pUbiNptII(s) | 2 |
| Q208 | 0 Days | 16.7 g | pUbiNptII(s) | 0 |
| KQ228 | Control | 1 plate (Approx 1 g) | Untransformed Control | Normal Regeneration >20 Plants |
| KQ228 | 35 Days | 20 g | pUbiNptII(s) | 9 |
| KQ228 | 28 Days | 20 g | pUbiNptII(s) | 6 |
| KQ228 | 22 Days | 20 g | pUbiNptII(s) | 10 |
| KQ228 | 13 Days | 20 g | pUbiNptII(s) | 11 |
| KQ228 | 6 Days | 20 g | pUbiNptII(s) | 24 |
| KQ228 | 0 Days | 17.6 g | pUbiNptII(s) | 100% Contaminated |
| Q232 | Control | 1 plate (Approx 1 g) | Untransformed Control | Med Regeneration >15 Plants |
| Q232 | 35 Days | 20 g | pUbiNptII(s) | 0 |
| Q232 | 28 Days | 20 g | pUbiNptII(s) | 0 |
| Q232 | 22 Days | 20 g | pUbiNptII(s) | 2 |
| Q232 | 13 Days | 20 g | pUbiNptII(s) | 1 |
| Q232 | 6 Days | 20 g | pUbiNptII(s) | 2 |
| Q232 | 0 Days | 17.7 g | pUbiNptII(s) | 0 |

The data for four different sugar can varieties shows that use of young callus in transformation procedures results in an increased number of transformation events as compared the number of events achieved with older callus, which is standard in the art (Joyce et al. *Plant Cell Rep.* 29:173-183 (2010); Elliott et al. *Austral. J. Plant Physiol.* 25:739-743 (1998)).

It is noted that the variety Q117, which is a variety of sugar cane that is relatively easy to transform, also responds to the use of younger callus than that which is traditionally used (i.e., 8 week to 10 week-old callus tissue). Varieties that are more recalcitrant to transformation (e.g., Q232) are particularly responsive to the use of young callus (e.g., less than 28 days old post-initiation).

These data show that the use of younger callus (e.g., less than 28 days old) than that which is standard in the art (8-10 weeks) (Joyce et al. *Plant Cell Rep.* 29:173-183 (2010); Elliott et al. *Austral. J. Plant Physiol.* 25:739-743 (1998)) can be useful for all sugar cane varieties, but it is particularly useful with varieties that are more difficult to transform such as Q208 and Q232. Thus, the methods of the present invention may make some commercially important, but more recalcitrant, varieties now amenable to transformation or higher transformation efficiency. The sugar cane varieties that were previously avoided due to the difficulty in obtaining transgenic events using conventional callus production system can now be utilized as genetic material using the methods of the present invention.

All publications and patent applications mentioned in the specification are indicative of the level of skill of those skilled in the art to which this invention pertains. Further, all publications, patent applications, patents and other references cited herein are incorporated by reference in their entireties for the teachings relevant to the sentence and/or paragraph in which the reference is presented.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. A method of stably transforming a sugar cane callus tissue or a cell thereof, the method comprising:
    (a) inoculating a sugar cane callus tissue or a cell thereof that is from about 6 days to about 14 days post-initiation with *Agrobacterium* comprising a nucleotide sequence of interest, to produce an *Agrobacterium*-inoculated sugar cane callus tissue or cell thereof; and
    (b) co-cultivating the *Agrobacterium*-inoculated sugar cane callus tissue or a cell thereof to produce a stably transformed sugar cane callus tissue or cell thereof, wherein the sugar cane callus tissue or cell thereof is from a sugar cane variety of Q117, KQ228, Q208 or Q232.

2. The method of claim 1, wherein the co-cultivating of the *Agrobacterium*-inoculated sugar cane callus tissue or cell thereof is carried out on a surface in the absence of co-culture medium for a time period sufficient to reduce the weight of said *Agrobacterium*-inoculated sugar cane callus tissue or cell thereof.

3. The method of claim 2, wherein said co-cultivating comprises culturing said *Agrobacterium*-inoculated sugar cane callus tissue or cell thereof on at least one layer of dry paper, wherein the paper is periodically changed during the co-cultivation.

4. The method of claim 1, further comprising regenerating a transformed sugar cane plant from the transformed sugar cane callus tissue or cell thereof.

* * * * *